(12) United States Patent
Croft et al.

(10) Patent No.: US 9,301,994 B2
(45) Date of Patent: Apr. 5, 2016

(54) LIGHT INHIBITORS FOR ASTHMA, LUNG AND AIRWAY INFLAMMATION, RESPIRATORY, INTERSTITIAL, PULMONARY AND FIBROTIC DISEASE TREATMENT

(75) Inventors: Michael Croft, San Diego, CA (US); Taylor Doherty, San Diego, CA (US); Shahram Salek-Ardakani, San Diego, CA (US)

(73) Assignee: La Jolla Institute for Allergy and Immunology, La Jolla, CA (US)

( * ) Notice: Subject to any disclaimer, the term of this patent is extended or adjusted under 35 U.S.C. 154(b) by 1207 days.

(21) Appl. No.: 13/010,670

(22) Filed: Jan. 20, 2011

(65) Prior Publication Data
US 2011/0150785 A1   Jun. 23, 2011

Related U.S. Application Data

(62) Division of application No. 12/233,428, filed on Sep. 18, 2008, now abandoned.

(60) Provisional application No. 60/973,383, filed on Sep. 18, 2007.

(51) Int. Cl.
*A61K 38/19* (2006.01)
*A61K 31/00* (2006.01)

(52) U.S. Cl.
CPC ............ *A61K 38/191* (2013.01); *A61K 31/00* (2013.01)

(58) Field of Classification Search
None
See application file for complete search history.

(56) References Cited

U.S. PATENT DOCUMENTS

| | | | | |
|---|---|---|---|---|
| 8,338,376 B2 * | 12/2012 | Beckman et al. | ............ | 514/16.6 |
| 2002/0001585 A1 * | 1/2002 | Browning et al. | ......... | 424/143.1 |
| 2003/0060605 A1 * | 3/2003 | Ware | ......................... | 530/388.3 |

FOREIGN PATENT DOCUMENTS

| | | | |
|---|---|---|---|
| EP | 1 336 619 A2 | | 8/2003 |
| EP | 1 336 619 A3 | | 10/2003 |
| WO | WO 2004/024076 A2 | | 3/2004 |
| WO | WO 2006/054961 A2 | | 5/2006 |

OTHER PUBLICATIONS

An et al., Pharmacological Research 52 (2005) 234-244.*
An et al., Biol. Pharm. Bull. 29(10) 2025-2030 (2006).*
Browning J., Immunological Reviews 2008, vol. 223: 202-220.*
Columba-Cabezas et al., Journal of Neuroimmunology 179 (2006) 76-86.*
Doherty et al., 2011, Nature Medicine 17: 596-604.*
Dohi et al., J Immunol 2001; 167:2781-2790.*
Fava et al., J Immunol 2003; 171:115-126.*
Genovese, M.C., et al; Arthritis Rheum 2009; 60 Suppl 10:417.*
Huang Z., Pharmacology & Therapeutics 86 (2000) 201-215.*
Levisetti et al., Diabetes 53: 3115-3119, 2004.*
Biogen Idec, Dec. 2007, ClinicalTrials.gov Identifier: NCT00292422.*
Plant et al., The Journal of Neuroscience, Jul. 11, 2007, 27(28):7429-7437.*
Shao et al., Eur. J. Immunol. 2003. 33: 1736-1743.*
Spahn et al., Gastroenterology 2004;127:1463-1473.*
Stopfer et al., Clin Exp Immunol 2004; 136: 21-29.*
Wu et al., J. Exp. Med., vol. 193, No. 11, Jun. 4, 2001 1327-1332.*
Kwon, B., et al., Involvement of Tumor Necrosis Factor Receptor Superfamily (TNFRSF) Members in the Pathogenesis of Inflammatory Diseases, Experimental and Molecular Medicine, 2003, 35(1):8-16.
Ware, C.F., Targeting Lymphocyte Activation Through the Lymphotoxin and LIGHT Pathways, Immunological Reviews, 2008, 223(1):186-201.
International Application No. PCT/US2008/076903, International Search Report and Written Opinion mailed Oct. 13, 2009.
Doherty, Taylor A., et al., The Tumor Necrosis Factor Family Member LIGHT is a Target for Asthmatic Airway Remodeling, Nature Medicine, 2011, 17(5):596-603.

* cited by examiner

*Primary Examiner* — Ilia Ouspenski
(74) *Attorney, Agent, or Firm* — Pillsbury Winthrop Shaw Pittman LLP

(57) ABSTRACT

Methods of treating inflammatory conditions, disease and disorders are provided. Method include, for example, contacting or administering a sufficient amount of a LIGHT inhibitor to a subject to treat the inflammatory condition, disease or disorder.

21 Claims, 7 Drawing Sheets

Fig. 2
a)
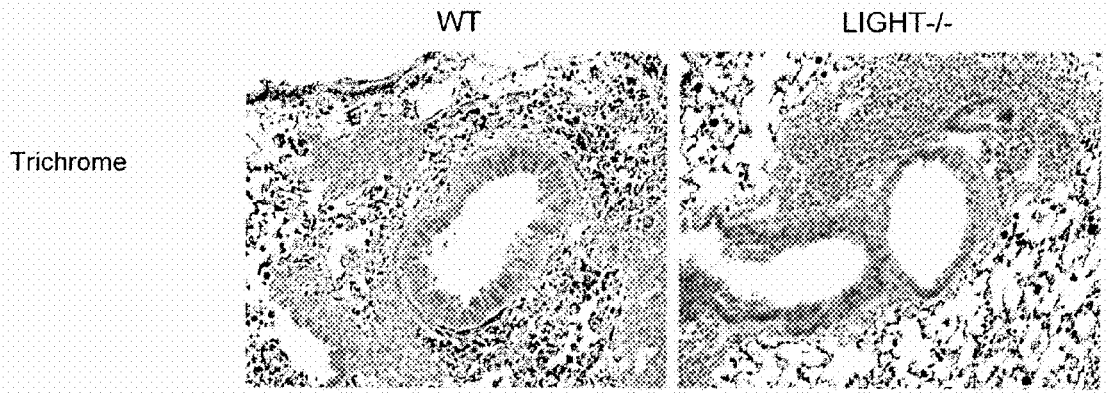
Trichrome
Smooth muscle actin
b)
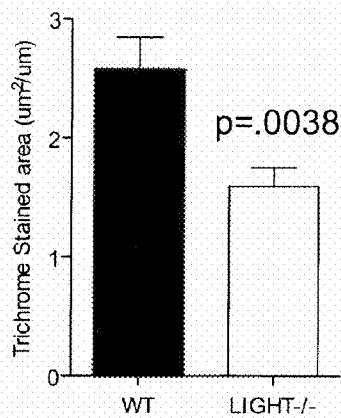
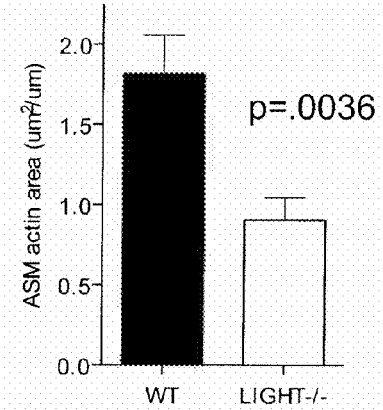

Fig. 5
A.
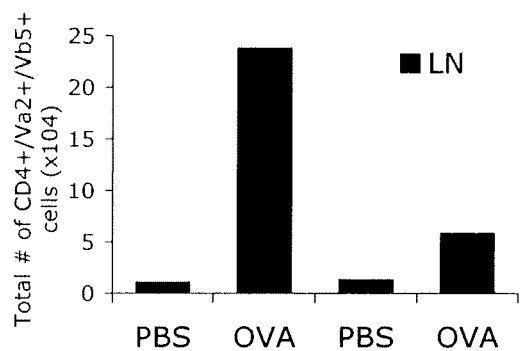
B.
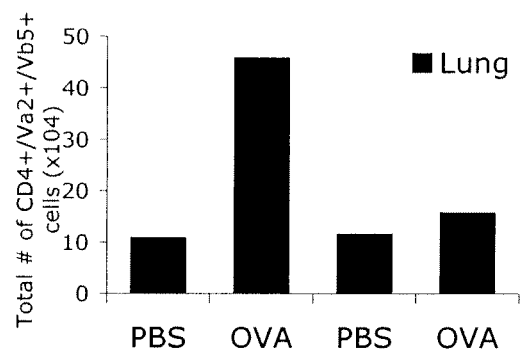

Fig. 6
a) WT OTII->WT | LIGHT-/- OTII->WT | BAL Vα2β5
BAL 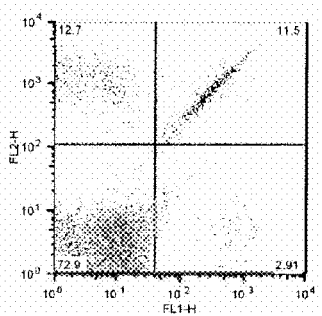 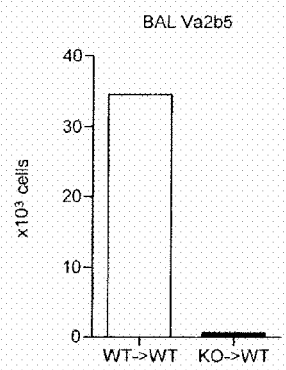
b) Lung Vα2β5
Lung 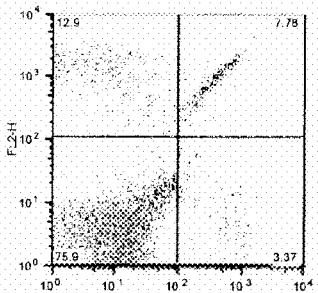 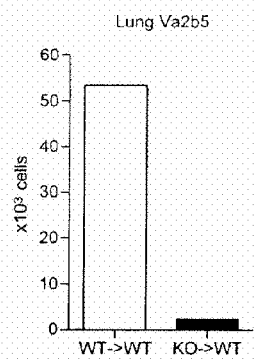
c) LN Vα2β5
LDLN 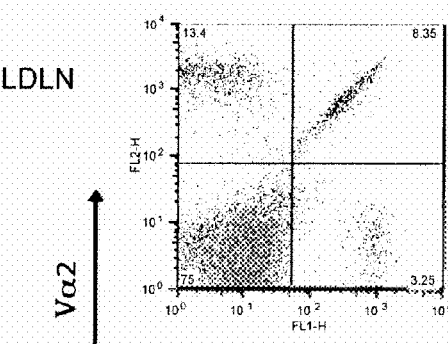 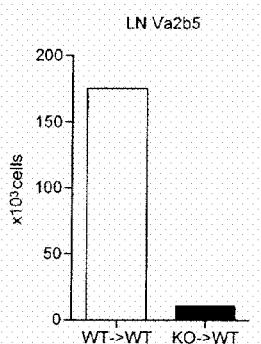
Vα2 ↑
Vβ5 →

Fig. 7
a)
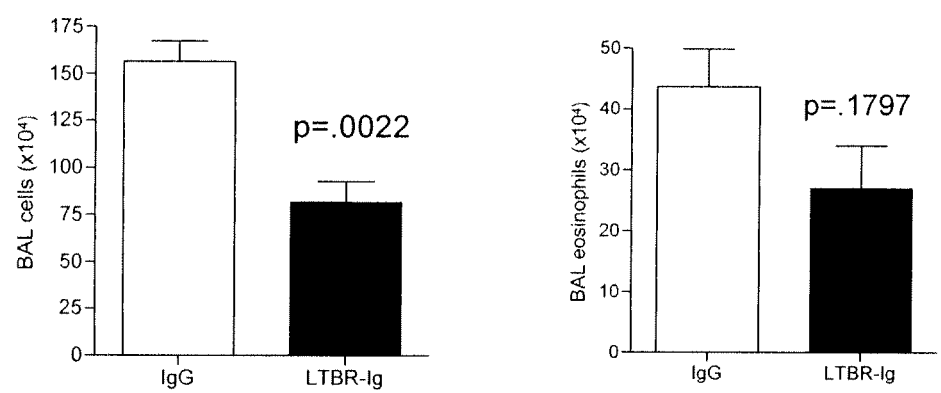
b)
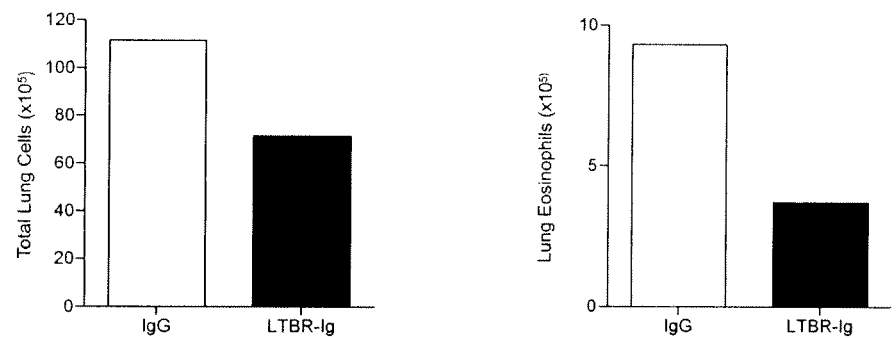

LIGHT INHIBITORS FOR ASTHMA, LUNG AND AIRWAY INFLAMMATION, RESPIRATORY, INTERSTITIAL, PULMONARY AND FIBROTIC DISEASE TREATMENT

RELATED APPLICATIONS

This application is a divisional of U.S. patent application Ser. No. 12/233,428, filed Sep. 18, 2008 now abandoned and which claimed the benefit of U.S. Provisional Application Serial No. 60/973,383, filed Sep. 18, 2007, all of which applications are expressly incorporated herein by reference in its entirety.

STATEMENT AS TO FEDERALLY SPONSORED RESEARCH

The invention was supported in part by National Institute of Health RO1 Grant AI070535. The government may have certain rights in the invention.

INTRODUCTION

Allergic asthma afflicts 10 million people in the US and is responsible for approximately five thousand deaths annually. The prevalence of asthma has significantly increased over the past few decades along with other allergic diseases, which are characterized by helper T cell 2 (Th2) responses. Current therapy primarily includes corticosteroids, bronchodilators, and leukotriene antagonists. A subset of those with more severe disease have a progressive decline in lung function attributed to airway remodeling which includes bronchial epithelial mucus metaplasia, airway smooth muscle hypertrophy/hyperplasia, subepithelial fibrosis, and increased angiogenesis. Current asthma treatment has little impact, if any, on airway remodeling.

Inflammatory cells including T cells, eosinophils, macrophages, and mast cells, as well as structural cells including epithelial, smooth muscle, and fibroblasts have roles in the establishment and maintenance of remodeling. Growth factors and cytokines that regulate remodeling include TGF-β, VEGF, IL-5, IL-9, IL-13, and eotaxin. An understanding of novel mechanisms may lead to much needed therapies that target airway remodeling and Th2 driven lung inflammation.

LIGHT (TNFSF14, p30 polypeptide) is a protein expressed on activated CD4/CD8 T cells, dendritic cells (DCs), monocytes, and natural killer cells (NK). The binding of LIGHT to herpes virus entry mediator (HVEM), which is expressed on resting T cells, DCs, and monocytes, or the lymphotoxin beta receptor (LTβR), which is expressed on DCs and stromal cells, promotes T cell activation, proliferation, and cytokine production. Studies have determined that LIGHT deficient animals have no significant abnormalities in the development of lymphoid organs and lymphocytes.

SUMMARY

The invention is based at least in part on the finding that LIGHT (P30 polypeptide), a TNF superfamily protein expressed on activated T cells, and other immune cells such as dendritic cells, controls the development of airway remodeling and TH2 driven lung responses. Inhibiting or blocking LIGHT from interacting with its receptors, HVEM or LTβR, can be used as an anti-inflammatory, for example, to inhibit or suppress asthmatic inflammation, as well as treat airway remodeling, among other inflammatory conditions, diseases and disorders. In addition, inhibiting or blocking LIGHT from interacting with its receptors, HVEM or LTβR, is applicable towards a wide range of chronic and acute fibroproliferative diseases of the lung and airways, including pulmonary fibrosis and COPD (chronic obstructive pulmonary disease), and other tissue and organ systems.

In accordance with the invention, there are provided, methods of reducing or inhibiting lung or airway inflammation (chronic or acute). In one embodiment, a method includes contacting or administering a sufficient amount of an inhibitor of LIGHT (p30 polypeptide) to a subject in need thereof to reduce or inhibit lung or airway inflammation in the subject.

In accordance with the invention, there are also provided, methods of treating asthma. In one embodiment, a method includes contacting or administering a sufficient amount of an inhibitor of LIGHT (p30 polypeptide) to a subject in need thereof to treat asthma.

In accordance with the invention, there are further provided, methods for treating a respiratory, interstitial, pulmonary disease or disorder, and fibrotic diseases and disorders (chronic or acute). In one embodiment, a method includes contacting or administering a sufficient amount of an inhibitor of LIGHT (p30 polypeptide) to a subject to treat the respiratory, interstitial, or pulmonary disease or disorder, or the fibrotic disease or disorder.

LIGHT inhibitors include, for example, molecules that bind to LIGHT and inhibit LIGHT binding or interaction with HVEM. LIGHT inhibitors also include molecules that bind to LIGHT and inhibit LIGHT binding or interaction with LTβR. LIGHT inhibitors further include molecules that bind to HVEM and inhibit LIGHT binding or interaction with HVEM. LIGHT inhibitors additionally include molecules that bind to LTβR and inhibit LIGHT binding or interaction with LTβR. LIGHT inhibitors moreover include prodrugs of the foregoing.

Invention methods include contact or administration, in vitro, ex vivo or in vivo (e.g., to a subject in need of treatment). In various embodiments, lung or airway inflammation, asthma, or a symptom caused by or associated with respiratory, interstitial, or pulmonary disease or disorder, or the fibrotic disease or disorder is reduced, decreased, inhibited, delayed, halted, or prevented in the subject, locally, or regionally in an area (region), tissue or organ of the subject. In particular aspects, a symptom is reduced, decreased, inhibited, delayed, halted, or prevented in a respiratory, interstitial or pulmonary tissue or organ. In another aspect, a method reduces, decreases, inhibits, delays, halts, or prevents inflammation or constriction of lung, airways or respiratory mucosum. In yet another embodiment, contacting or administration in vivo is in a subject that has previously experienced an asthmatic episode or airway- or broncho-constriction or is in need of airway- or broncho-dilation.

In accordance with the invention, there are also provided, methods of inhibiting, reducing or decreasing progression, severity, frequency, duration or probability of one or more symptoms caused by or associated with lung or airway inflammation or asthma. In one embodiment, a method includes administering to a subject an amount of a LIGHT inhibitor sufficient to inhibit, reduce or decrease progression, severity, frequency, duration or probability of a symptom associated with lung or airway inflammation or asthma. In various aspects, asthma is caused by an allergen or by exercise.

Symptoms include, for example, lung, airway or respiratory mucosum inflammation or tissue damage or remodeling, shortness of breath (dyspnea), rapid breathing (tachypnea), wheezing, stridor, coughing, decreased or reduced lung capacity, chest-tightness, chest pain, prolonged expiration, increased heart rate (tachycardia), runny nose, airway-constriction, decreased lung capacity, or an acute asthmatic episode, or infiltration of a lung or pulmonary or lymphatic tissue (draining lymph nodes), lymph nodes or airway with immune cells, such as leukocytes and eosinophils, hyperplasia of mucus secreting epithelium, inflammatory lesion of lung, goblet cell hyperplasia, or increased Th2 cytokine production (e.g., an interleukin such as IL-4, IL-5, IL-9, IL-13, IL-16, IL-17 or IL-25).

Respiratory diseases can affect the upper or lower respiratory tract. Non-limiting examples include asthma, allergic asthma, bronchiolitis and pleuritis. Additional non-limiting examples include allergic disorders, such as Extrinsic bronchial asthma; Allergic rhinitis; Onchocercal dermatitis; Atopic dermatitis, Drug reactions; Nodules, eosinophilia, rheumatism, dermatitis, and swelling (NERDS); Eosophageal and gastrointestinal allergies. Further non-limiting examples include Airway Obstruction, Apnea, Asbestosis, Atelectasis, Berylliosis, Bronchiectasis, Bronchiolitis, Bronchiolitis Obliterans, Organizing Pneumonia, Bronchitis, Bronchopulmonary Dysplasia, Common Cold, Cough, Empyema, Pleural Empyema, Pleural Epiglottitis, Hemoptysis, Hypertension, Kartagener Syndrome, Meconium Aspiration, Pleural Effusion, Pleurisy, Pneumonia, Pneumothorax, Respiratory Distress Syndrome, Respiratory Hypersensitivity, Respiratory Tract Infections, Rhinoscleroma, Scimitar Syndrome, Severe Acute Respiratory Syndrome, Silicosis, Tracheal Stenosis and Whooping Cough. Still further non-limiting examples of respiratory diseases include influenza.

In another embodiment, a method includes administering an amount sufficient to inhibit, reduce or decrease progression, severity, frequency, probability, duration or prevent one or more adverse physiological or psychological symptoms caused by or associated with a chronic or acute condition, disorder or disease caused by or associated with undesirable or abnormal lung or airway inflammation, asthma, or a respiratory, interstitial, or pulmonary disease or disorder. In particular aspects, a condition, disorder or disease is allergic asthma, an acute asthmatic episode, airway constriction, or lung or airway inflammation, or a respiratory, interstitial, or pulmonary disease or disorder.

Invention treatment methods include providing a given subject with an objective or subjective improvement of the condition, disorder or disease, a symptom caused by or associated with the condition, disorder or disease, or the probability or susceptibility of a subject to the condition or a symptom caused by or associated with the condition, disorder or disease. In various embodiments, treatment reduces, decreases, inhibits, delays, eliminates or prevents the probability, susceptibility, severity, frequency, or duration of one or more symptoms caused by or associated with the condition, disorder or disease. In a particular aspect, a method inhibits, reduces or decreases the probability, severity, frequency, duration or preventing a subject from having an acute asthmatic episode (e.g., an acute asthmatic episode caused by an allergen, allergic asthma or excercise). In another particular aspect, a method reduces the probability, severity, frequency, duration or delays, halts, or prevents airway-constriction. In additional aspects, treatment improves or increases airway-dilation. In further aspects, a treatment improves asthma, reduces or inhibits lung or airway inflammation, or reduces or inhibits a symptom caused by or associated with a respiratory, interstitial, or pulmonary disease or disorder.

Candidate subjects for methods of the invention include mammals, such as humans. Candidate subjects for methods of the invention also include subjects that are in need of treatment, e.g., any subject that may benefit from a treatment. Candidate subjects for methods of the invention therefore include subjects that have or are at risk of having a condition, disorder or disease caused by or associated with asthma, lung or airway inflammation, or a respiratory, interstitial, or pulmonary disease or disorder. In particular aspects, a subject has been diagnosed as having asthma, lung or airway inflammation, or a respiratory, interstitial, or pulmonary disease or disorder, or is at risk of having asthma, lung or airway inflammation, or a respiratory, interstitial, or pulmonary disease or disorder.

Methods of the invention can be practiced by administration or contact with any dose amount, frequency, delivery route or timing of a LIGHT inhibitor. In particular embodiments, a subject is administered or contacted a LIGHT inhibitor one, two, three, four or more times hourly, daily, bi-weekly, weekly, monthly or annually. In additional embodiments, an amount administered is about 0.00001 mg/kg, to about 10,000 mg/kg, about 0.0001 mg/kg, to about 1000 mg/kg, about 0.001 mg/kg, to about 100 mg/kg, about 0.01 mg/kg, to about 10 mg/kg, about 0.1 mg/kg, to about 1 mg/kg body weight, one, two, three, four, or more times per hour, day, bi-weekly, week, month or annually. In further embodiments, the amount administered is less than about 0.00001 mg/kg, one, two, three, four, or more times per hour, day, bi-weekly, week, month or annually. In particular aspects, the amount is administered substantially contemporaneously with, or within about 1-60 minutes, hours, or days of the onset of a symptom caused by or associated with asthma, lung or airway inflammation, or a respiratory, interstitial, or pulmonary disease or disorder.

Methods of the invention include routes of contact or administration of LIGHT inhibitor locally, regionally and systemically. In a particular embodiment, a LIGHT inhibitor is administered to achieve delivery to lungs, airways, or a lung, airway, respiratory, interstitial, or pulmonary area (region), tissue or organ.

Methods of the invention can be practiced in conjunction with one or more other treatment protocols or therapeutic regimens. In a particular embodiment, a method includes contacting or administering a second agent or drug to the subject prior to, with or following contacting or administering LIGHT inhibitor. In particular aspects, a second agent or drug includes an anti-inflammatory, anti-asthmatic or anti-allergy drug; a hormone or a steroid; an anti-histamine, anti-leukotriene, anti-IgE, anti-α4 integrin, anti-β2 integrin, anti-CCR3 antagonist, β2 agonist or an anti-selectin.

Invention compositions can be formulated as appropriate for practice of the methods. In one embodiment, a composition includes a LIGHT inhibitor, and a pharmaceutically acceptable carrier. In a particular aspect, the carrier is a physiologically acceptable gas, liquid, dry powder or an aerosol. In an additional particular aspect, the carrier is a capable of traversing into a lung or airway area (region),tissue or organ, an interstitial, or pulmonary area (region), tissue or organ, or a mucosal area (region), tissue or organ, or epithelium thereof. In a further particular aspect, the carrier is lipophilic or non-lipophilic.

Invention compositions can also be included in articles of manufacture or kits appropriate for practice of the invention methods. In one embodiment, a LIGHT inhibitor is included in an article of manufacture. In one aspect, an article of manufacture is a container having disposed therein a LIGHT inhibitor. In particular aspects, a container comprises a canister having disposed therein contents comprising a LIGHT inhibitor, said contents under pressure. In another aspect, a container comprises an aerosol generator or a spray generator (e.g., an inhaler, nasal sprayer or nebulizer). Exemplary inhalers include metered dose and dry powder inhalers. In a further aspect, an article of manufacture is for delivery of LIGHT inhibitor to the lungs or airways, for example, an intubation tube or face mask.

In accordance with the invention, further provided are kits. In one embodiment, a kit includes a LIGHT inhibitor or prodrug thereof In a particular aspect, a kit includes a LIGHT inhibitor or prodrug thereof disposed in an article of manufacture for delivery of the LIGHT inhibitor or prodrug to lung, airways or a respiratory, interstitial, or pulmonary area (region), tissue or organ, optionally with instructions for administering said LIGHT inhibitor to a subject. In a particular aspect, a kit includes a second drug (e.g., an anti-inflammatory, anti-asthmatic or anti-allergy drug; a hormone or a steroid;an anti-histamine, anti-leukotriene, anti-IgE, anti-α4 integrin, anti-β2 integrin, anti-CCR3 antagonist, β2 agonist, anti-selectin or glucocorticoid; H1-receptor antagonist; or a xanthine drug). In more particular aspects, an anti-leukotriene is a cysteinyl-leukotriene (Cys-LT); a β2 agonist is a β2-adrenoceptor.

BRIEF DESCRIPTION OF DRAWINGS

FIGS. 2A-2B show reduced peribronchial fibrosis and smooth muscle mass in lungs of LIGHT-deficient mice after chronic challenge with antigen via the airways: A) lung sections stained with trichrome to measure fibrosis and for alpha-smooth muscle actin; and B) bar graphs representative of the area of fibrosis or smooth muscle quantified using image analysis with normalization for bronchial size.

FIGS. 5A-5B show LIGHT-deficient T cells are impaired in accumulating in the lung and lung-draining lymph nodes (LN) following acute exposure to inhaled antigen (OVA): A) a bar graph representing the LN results; and B) a graph representing the lung results.

FIGS. 6A-6C show LIGHT-deficient T cells do not survive in vivo after chronic exposure to repetitive allergen (OVA) challenge via the airways: A-C) percentages (left) and absolute numbers (right) of wild-type or LIGHT-deficient CD4 T cells expressing OVA-specific TCR Vα2Vβ5 found in A) Bronchoalveolar lavagae; B) Lung; and C) lung-draining lymph nodes (LDLN).

FIGS. 7A-7B show Eosinophilic lung inflammation is reduced after therapeutic treatment with a lymphotoxin beta receptor (LTBR) fusion protein given during chronic allergen challenge: A) Total infiltrating cells (left) and eosinophils (right) in bronchoalveolar lavage; and B) total infiltrating cells (left) and eosinophils (right) in lung tissue.

DETAILED DESCRIPTION

Figure 1:
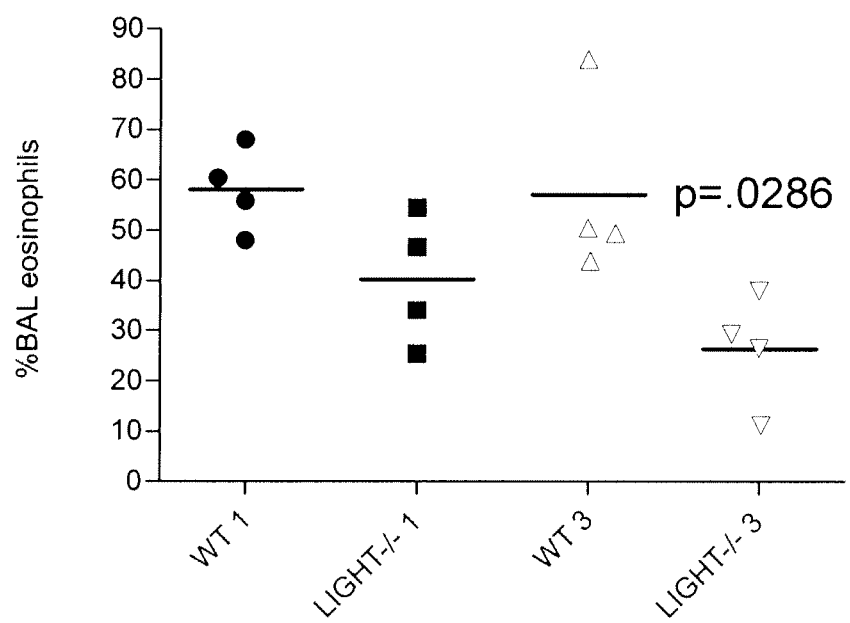
FIG. 1 shows reduced eosinophilic lung inflammation in LIGHT-deficient mice after chronic challenge with antigen via the airways. Percent of bronchoalveolar lavagae eosinophils at 1 day and 3 days after last airway challenge is shown in the graph. Data are mean eosinophils from 4 mice per group for each time point.

The invention provides methods of reducing or inhibiting lung or airway inflammation (chronic or acute). The invention also provides methods of treating asthma. The invention further provides methods for treating a respiratory, interstitial, pulmonary disease or disorder, and fibrotic diseases and disorders (chronic or acute). In various embodiments, a method includes contacting or administering a sufficient amount of an inhibitor of LIGHT (p30 polypeptide) to a subject to reduce or inhibit lung or airway inflammation, to treat asthma or to treat the respiratory, interstitial, or pulmonary disease or disorder, or the fibrotic disease or disorder.

The term "an inhibitor of LIGHT," means a molecule that directly or indirectly inhibits binding of LIGHT (p30 polypeptide) to HVEM or to LTβR. Inhibitors therefore include molecules that bind to LIGHT as well as molecules that bind to a LIGHT receptor or target. Since LIGHT (p30 polypeptide) can bind to a variety of receptors and targets, such as HVEM and LTβR, LIGHT (p30 polypeptide) inhibitors therefore include molecules that bind to LIGHT (p30 polypeptide), molecules that bind to HVEM, as well as molecules that bind to LTβR, which can thereby inhibit binding of LIGHT to HVEM, binding of LIGHT to LTβR, etc., either directly or indirectly.

A non-limiting representative example of human LIGHT (p30 polypeptide) sequence (SEQ ID NO:1; the amino acid residues of the transmembrane domain are shaded, and the amino acid residues of the extracellular domain are underlined) target for an inhibitor is as set forth below:

MEESVVRPSVFVVDGQTDIPFTRLGRSHRRQSCSVARVGLGLLLLLMGA

GLAVQGWFLLQLHWRLGEMVTRLPDGPAGSWEQLIQERRSHEVNPAAHL

TGANSSLTGSGGPLLWETQLGLAFLRGLSYHDGALVVTKAGYYYIYSKV

QLGGVGCPLGLASTITHGLYKRTPRYPEELELLVSQQSPCGRATSSSRV

WWDSSFLGGVVHLEAGEEVVVRVLDERLVRLRDGTRSYFGAFMV

A non-limiting representative example of human HVEM (herpesvirus entry mediator) sequence target for an inhibitor, also referred to as tumor necrosis factor receptor superfamily, member 14 (TNFRSF14) is as set forth below (SEQ ID NO:2):

MEPPGDWGPPPWRSTPKTDVLRLVLYLTFLGAPCYAPALPSCKEDEYPV

GSECCPKCSPGYRVKEACGELTGTVCEPCPPGTYIAHLNGLSKCLQCQM

CDPAMGLRASRNCSRTENAVCGCSPGHFCIVQDGDHCAACRAYATSSPG

QRVQKGGTESQDTLCQNCPPGTFSPNGTLEECQHQTKCSWLVTKAGAGT

SSSHWVWWFLSGSLVIVIVCSTVGLIICVKRRKPRGDVVKVIVSVQRKR

QEAEGEATVIEALQAPPDVTTVAVEETIPSFTGRSPNH

A non-limiting representative example of human LTβR sequence target for an inhibitor, is as set forth below (SEQ ID NO:3):

```
MLLPWATSAPGLAWGPLVLGLFGLLAASQPQAVPPYASENQTCRDQEKE

YYEPQHRICCSRCPPGTYVSAKCSRIRDTVCATCAENSYNEHWNYLTIC

QLCRPCDPVMGLEEIAPCTSKRKTQCRCQPGMFCAAWALECTHCELLSD

CPPGTEAELKDEVGKGNNHCVPCKAGHFQNTSSPSARCQPHTRCENQGL

VEAAPGTAQSDTTCKNPLEPLPPEMSGTMLMLAVLLPLAFFLLLATVFS

CIWKSHPSLCRKLGSLLKRRPQGEGPNPVAGSWEPPKAHPYFPDLVQPL

LPISGDVSPVSTGLPAAPVLEAGVPQQQSPLDLTREPQLEPGEQSQVAH

GTNGIHVTGGSMTITGNIYIYNGPVLGGPPGPGDLPATPEPPYPIPEEG

DPGPPGLSTPHQEDGKAWHLAETEHCGATPSNRGPRNQFITHD
```

Exemplary LIGHT inhibitors include, for example, small organic compounds (e.g., drugs), polypeptide sequences such as antibodies and antibody subsequences that bind to LIGHT (p30 polypeptide), HVEM (herpesvirus entry mediator) or LTβR (lymphotoxin beta receptor). Additional exemplary LIGHT inhibitors include, for example, a LIGHT, HVEM or LTβR (lymphotoxin beta receptor) polypeptide subsequence, variant sequence, chimeric sequence or dominant negative sequence (e.g., soluble forms of LIGHT, HVEM or LTβR). Further exemplary LIGHT inhibitors include, for example, chimeric sequences, such as a fusion of a LIGHT, HVEM or LTβR polypeptide sequence (e.g., soluble forms of LIGHT, HVEM or LTβR) and an immunoglobulin (Ig) sequence.

Exemplary LIGHT antibodies include, for example, antibodies that bind to human LIGHT. Non-limiting examples of commercially available antibodies that bind to human LIGHT include clone T5-39 (BioLegend, San Diego, Calif.), clone 115520 (R&D Systems, Minneapolis, Minn.), clones A-20 and C-20 (Santa Cruz Biotech, Santa Cruz, Calif.), and clone 4E3 (Novus Biologicals, Inc., Littleton, Colo.).

Antibodies include mammalian, human, humanized, humaneered or primatized forms of heavy or light chain, $V_H$ and $V_L$, respectively, immunoglobulin (Ig) molecules. An "antibody" means any monoclonal or polyclonal immunoglobulin molecule, such as IgM, IgG, IgA, IgE, IgD, and any subclass thereof, which includes intact immunoglobulin molecules, two full length heavy chains linked by disulfide bonds to two full length light variable domains, $V_H$ and $V_L$, individually or in any combination, as well as subsequences, such as Fab, Fab', (Fab')$_2$, Fv, Fd, scFv and sdFv, unless otherwise expressly stated.

An antibody that binds to LIGHT, HVEM or LTβR antibody means that the antibody has affinity for LIGHT, HVEM or LTβR. "Specific binding" is where the binding is selective between the two referenced molecules. Thus, specific binding of an antibody for LIGHT, HVEM or LTβR is that which is selective for an epitope present in LIGHT, HVEM or LTβR. Typically, specific binding can be distinguished from non-specific when the dissociation constant ($K_D$) is less than about $1\times10^{-5}$ M or less than about $1\times10^{-6}$ M or $1\times10^{-7}$ M. Selective binding can be distinguished from non-selective binding using assays known in the art (e.g., immunoprecipitation, ELISA, Western blotting) with appropriate controls.

Monoclonal antibodies are made by methods known in the art (Kohler et al., *Nature*, 256:495(1975); and Harlow and Lane, *Using Antibodies: A Laboratory Manual*, Cold Spring Harbor Laboratory, 1999). Briefly, monoclonal antibodies can be obtained by injecting mice with antigen. The polypeptide or peptide used to immunize an animal may be derived from translated DNA or chemically synthesized and conjugated to a carrier protein. Commonly used carriers which are chemically coupled to the immunizing peptide include, for example, keyhole limpet hemocyanin (KLH), thyroglobulin, bovine serum albumin (BSA), and tetanus toxoid. Antibody production is verified by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from hybridoma cultures. Monoclonal antibodies can be isolated and purified from hybridoma cultures by a variety of established techniques which include, for example, affinity chromatography with Protein-A Sepharose, size-exclusion chromatography, and ion-exchange chromatography (see e.g., Coligan et al., *Current Protocols in Immunology* sections 2.7.1-2.7.12 and sections 2.9.1-2.9.3; and Barnes et al., "Methods in Molecular Biology," 10:79-104, Humana Press (1992)).

A "human antibody" means that the amino acid sequence of the antibody is fully human, i.e., human heavy and light chain variable and constant regions. The antibody amino acids are coded for in the human DNA antibody sequences or exist in a human antibody. Fully human antibodies can be made by human antibody transgenic or transchromosomic animals, such as mice, or by isolation from human antibody producing cell lines (e.g., B cells) by recombinant DNA methodology known to the skilled artisan, such as gene cloning by reverse transcriptase polymerase chain reaction (RT-PCR). An antibody that is non-human may be made fully human by substituting non-human amino acid residues with amino acid residues that exist in a human antibody. Amino acid residues present in human antibodies, CDR region maps and human antibody consensus residues are known in the art (see, e.g., Kabat, *Sequences of Proteins of Immunological Interest*, 4th Ed. US Department of Health and Human Services. Public Health Service (1987); Chothia and Lesk, J. Mol. Biol. (1987) 186:651; Padlan Mol. Immunol. (1994) 31:169; and Padlan Mol. Immunol. (1991) 28:489). Methods of producing human antibodies are also described, for example, in WO 02/43478 and WO 02/092812.

The term "humanized," when used in reference to an antibody, means that the antibody sequence has non-human amino acid residues of one or more complementarity determining regions (CDRs) that specifically bind to the antigen in an acceptor human immunoglobulin molecule, and one or more human amino acid residues in the framework region (FR) that flank the CDRs. Any mouse, rat, guinea pig, goat, non-human primate (e.g., ape, chimpanzee, macaque, orangutan, etc.) or other animal antibody may be used as a CDR donor for producing humanized antibody. Human framework region residues can be replaced with corresponding non-human residues (e.g., from the donor variable region). Residues in the human framework regions can therefore be substituted with a corresponding residue from the non-human CDR donor antibody. A humanized antibody may include residues, which are found neither in the human antibody nor in the donor CDR or framework sequences. The use of antibody components derived from humanized monoclonal antibodies reduces problems associated with the immunogenicity of non-human regions. Methods of producing humanized antibodies are known in the art (see, for example, U.S. Pat. Nos. 5,225,539; 5,530,101, 5,565,332 and 5,585,089; Riechmann et al., (1988) Nature 332:323; EP 239,400; W091/09967; EP 592,106; EP 519,596; Padlan Molecular Immunol. (1991) 28:489; Studnicka et al., Protein Engineering (1994) 7:805; Singer et al., J. Immunol. (1993) 150:2844; and Roguska et al., Proc. Nat'l. Acad. Sci. USA (1994) 91:969).

The term "humaneered," when used in reference to an antibody, means that the antibody sequence has high affinity for antigen but has a greater number of human germline sequences than a humanized antibody. Typically humaneered antibody has at least 90% or more human germline sequences.

As used herein, the terms "peptide," "polypeptide" and "protein" are used interchangeably and refer to two or more amino acids covalently linked by an amide bond or non-amide equivalent. Polypeptides include full length native polypeptide, and "modified" forms such as subsequences, variant sequences, fusion/chimeric sequences and dominant-negative sequences.

Peptides include L- and D-isomers, and combinations thereof. Peptides can include modifications typically associated with post-translational processing of proteins, for example, cyclization (e.g., disulfide or amide bond), phosphorylation, glycosylation, carboxylation, ubiquitination, myristylation, or lipidation. Modified peptides can have one or more amino acid residues substituted with another residue, added to the sequence or deleted from the sequence. Specific examples include one or more amino acid substitutions, additions or deletions (e.g., 1-3, 3-5, 5-10, 10-20, or more).

Subsequences and fragments refer to polypeptides having one or more fewer amino acids in comparison to a reference (e.g., native) polypeptide sequence. An antibody subsequence that specifically binds to LIGHT, HVEM or LTβR can retain at least a part of its binding or LIGHT inhibitory or antagonist activity.

A variant peptide can have a sequence with 50%, 60%, 70%, 75%, 80%, 85%, 90%, 95%, 96%, 97%, 98%, or more identity to a reference sequence. Variant sequences include naturally occurring alterations of sequence, due to intra-species polymorphisms or different species, as well as artificially produced alterations of sequence. Sequence homology between species is in the range of about 70-80%. An amino acid substitution is one example of a variant.

A "conservative substitution" is the replacement of one amino acid by a biologically, chemically or structurally similar residue. Biologically similar means that the substitution is compatible with an activity or function of the unsubstituted sequence. Structurally similar means that the amino acids have side chains with similar length, such as alanine, glycine and serine, or having similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

Peptides synthesized and expressed as fusion proteins have one or more additional domains linked thereto, and are also referred to as chimeric polypeptides. The additional domain(s) may confer an additional function upon the sequence. For example, HVEM-IgG or LTβR-IgG fusion proteins can have LIGHT inhibitory activity.

The term "fusion," when used in reference to two or more molecules (e.g., polypeptides) means that the molecules are covalently attached. A particular example for attachment of two protein sequences is an amide bond or equivalent. The term "chimeric," and grammatical variations thereof, when used in reference to a protein, means that the protein is comprised of one or more heterologous amino acid residues from one or more different proteins.

The term "heterologous," when used in reference to a polypeptide, means that the polypeptide is not normally contiguous with the other polypeptide in its natural environment. Thus, a chimeric polypeptide means that a portion of the polypeptide does not exist fused with the other polypeptide in normal cells. In other words, a chimeric polypeptide is a molecule that does not normally exist in nature, i.e., such a molecule is produced by the hand of man, e.g., artificially produced through recombinant DNA technology.

As used herein, the term "mimetic" refers to a synthetic chemical compound which has substantially the same structural and/or functional characteristics as the reference molecule. The mimetic can be entirely composed of synthetic, non-natural amino acid analogues, or can be a chimeric molecule including one or more natural peptide amino acids and one or more non-natural amino acid analogs. The mimetic can also incorporate any number of natural amino acid conservative substitutions as long as such substitutions do not destroy activity.

Peptide mimetics can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., induce or stabilize a secondary structure, e.g., a beta turn, gamma turn, beta sheet, alpha helix conformation, and the like. For example, a polypeptide can be characterized as a mimetic when one or more of the residues are joined by chemical means other than an amide bond. Individual peptidomimetic residues can be joined by amide bonds, non-natural and non-amide chemical bonds other chemical bonds or coupling means including, for example, glutaraldehyde, N-hydroxysuccinimide esters, bifunctional maleimides, N,N'-dicyclohexylcarbodiimide (DCC) or N,N'-diisopropyl-carbodiimide (DIC). Linking groups alternative to the amide bond include, for example, ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins*, Vol. 7, pp 267-357, "Peptide and Backbone Modifications," Marcel Decker, NY).

Peptides and peptidomimetics can be produced and isolated using a variety of methods known in the art. Full length peptides and fragments (subsequences) can be synthesized using chemical methods known in the art (see, e.g., Caruthers, Nucleic Acids Res. Symp. Ser. (1980) 215; Horn, Nucleic Acids Res. Symp. Ser. (1980) 225; and Banga, A. K., Therapeutic Peptides and Proteins, Formulation, Processing and Delivery Systems (1995) Technomic Publishing Co., Lancaster, Pa.). Peptide synthesis can be performed using various solid-phase techniques (see, e.g., Roberge, Science (1995) 269:202; Merrifield, Methods Enzymol. (1997) 289:3). Automated synthesis may be achieved, e.g., using a peptide synthesizer.

Individual synthetic residues and polypeptides incorporating mimetics can be synthesized using a variety of procedures and methodologies known in the art (see, e.g., Organic Syntheses Collective Volumes, Gilman, et al. (Eds) John Wiley & Sons, Inc., NY). Peptides and peptide mimetics can also be synthesized using combinatorial methodologies. Techniques for generating peptide and peptidomimetic libraries are known, and include, for example, multipin, tea bag, and split-couple-mix techniques (see, for example, al-Obeidi, Mol. Biotechnol. (1998) 9:205; Hruby, Curr. Opin. Chem. Biol. (1997) 1:114; Ostergaard, Mol. Divers. (1997) 3:17; and Ostresh, Methods Enzymol. (1996) 267:220). Modified peptides can be further produced by chemical modification methods (see, e.g., Belousov, Nucleic Acids Res. (1997) 25:3440;

Frenkel, Free Radic. Biol. Med. (1995) 19:373; and Blommers, Biochemistry (1994) 33:7886).

Inhibitors of LIGHT therefore include those that can bind selectively as well as those that bind non-selectively to a ligand or target (e.g., LIGHT, HVEM, LTβR, etc.) in solution, in solid phase, in vitro, ex vivo or in vivo. As used herein, the term "selective" when used in reference to a LIGHT inhibitor, means that the inhibitor binds specifically to the target entity (e.g., LIGHT, HVEM, LTβR, etc.) and does not significantly bind to a non-ligand or non-target entity. A non-selective inhibitor means that the inhibitor is not selective for the entity to which it binds, i.e., it cross-reacts with other entities.

LIGHT inhibitors include variants and derivatives that retain at least a part or all of an activity of the non-variant or non-derivatized inhibitor. A particular activity (e.g., antagonist or inhibitory activity) of a LIGHT inhibitor may be less than or greater than the activity of a corresponding non-variant or non-derivatized LIGHT inhibitor. For example, a LIGHT inhibitor variant or derivative may have less or greater activity than non-variant or non-derivatized LIGHT inhibitor.

Non-limiting examples of activities that can be retained, at least in part, include inhibitory or antagonist activity, binding affinity (e.g., $K_d$), avidity and binding selectivity (specificity) or non-selectivity. The variant or derivatized inhibitor can exhibit an activity (e.g., binding affinity) that is greater or less than a corresponding non-variant or non-derivatized inhibitor, e.g., greater or less inhibitory activity, binding affinity (e.g., $K_d$), avidity or binding selectivity (specificity) or non-selectivity. For example, "at least a part" of an activity of an inhibitor can be when the variant or derivatized agent has less of an inhibitory activity, e.g., 10-25%, 25-50%, 50-60%, 60-70%, 70-75%, 75-80%, 80-85%, 85-90%, 90-95%, 95-99%, 100%, or any percent or numerical value or range or value within such ranges. An activity of an inhibitor can be when the variant or derivatized agent has more inhibitory activity, e.g., 110-125%, 125-150%, 150-175%, 175-200%, 200-250%, 250-300%, 300-400%, 400-500%, 500-1000%, 1000-2000%, 2000-5000%, or more, or any percent or numerical value or range or value within such ranges. At least a part of binding affinity of an inhibitor can be when the variant or derivatized inhibitor has less affinity, e.g., 1-3-fold, 1-5-fold, 2-5 fold, 5-10-fold, 5fold, 10-15-fold, 15-20-fold, 20-25-fold, 25-30-fold, 30-50-fold, 50-100 fold, 100-500-fold 500-1000-fold, 1000-5000-fold, or less (e.g., $K_d$), or any numerical value or range of values within such ranges. At least a part of binding affinity of an inhibitor can be when the variant or derivatized inhibitor has more affinity, e.g., 1-3-fold, 1-5-fold, 2-5 fold, 5-10-fold, 5-15-fold, 10-15-fold, 15-20-fold, 20-25-fold, 25-30-fold, 30-50-fold, 50-100 fold, 100-500-fold 500-1000-fold, 1000-5000-fold, or more (e.g., $K_d$), or any numerical value or range of values within such ranges.

LIGHT inhibitors can be identified by assays known in the art. For example, the amount of activity can be assessed directly, such as measuring the particular activity (e.g., inhibitor activity, binding affinity, avidity, selectivity (specificity) or non-selectivity). For example, a LIGHT inhibitor can be identified by inhibition of HVEM or LTR mediated lymphocyte activation or cell proliferation. A LIGHT inhibitor can also be identified by change in cell expression of a marker, such as ICAM expression. LIGHT inhibitors can further be identified by the ability to inhibit binding of purified LIGHT to purified HVEM or LTβR (or HVEM-IgG or LTβR-IgG fusion proteins), for example, when immobilized on a substrate (e.g., plastic) by ELISA, or when any of the molecules are transfected into cells that can be identified by labeling with the corresponding binding partner by flow cytometry.

More particularly, for ELISA assays, plate bound LIGHT can be pre-incubated with LIGHT specific inhibitory molecules and blockade of receptor fusion protein binding measured by detection of the binding of the Fe fusion protein or lack of binding. Blockade of cell surface associated LIGHT binding to receptors is assessed by pre-incubation of LIGHT inhibitory molecules with cell lines expressing LIGHT on the surface followed by addition of receptor Fc fusion proteins. Assessment of inhibition is measured by detection of binding of the receptor fusion proteins or lack of binding by flow cytometry. Inhibition of LIGHT signaling in vitro can be determined by inhibiting LIGHT mediated chemokine secretion from colonic epithelial cells (HT29).

As used herein, the term "the same," when used in reference to a LIGHT inhibitor means that the activity is within about 50% more than or less than the reference inhibitor. The term "substantially the same" when used in reference to inhibitor activity means that the activity is within about 100-500% (2-5-fold) or any percent value or range of percent values within such ranges, more than or less than the reference inhibitor. The same, when used in reference to binding affinity, means that the dissociation constant ($K_d$) is within about 1-5-fold, or any numerical value or range of values within such a range, of the referenced agent (e.g., 1-5 fold greater affinity or 1-5 fold less affinity than the reference agent).

The term "substantially the same" when used in reference to binding affinity, means that the dissociation constant ($K_d$) is within about 5 to 100 fold, or any numerical value or range of values within such a range, of the reference inhibitor (5-100 fold greater affinity or 5-100 fold less affinity than the reference inhibitor). The term "the same," when used in reference to association constant ($K_a$) is within about 1 to 5 fold, or any numerical value or range of values within such a range, of the reference inhibitor (within 1-5 fold greater or 1-5 fold less than the association constant, $K_a$). The term "substantially the same" when used in reference to association constant ($K_a$), means that the association constant is within about 5 to 100 fold greater or less, or any numerical value or range of values within such a range, than the association constant, $K_a$, of the reference inhibitor (5-100 fold greater or 5-100 fold less than the reference inhibitor).

Dissociation ($K_d$) constants can be measured using radiolabeled inhibitors in competitive binding assays with increasing amounts of unlabelled inhibitor to generate saturation curves. The target, ligand or receptor used in the binding assay (e.g., LIGHT, HVEM, or LTβR, etc.) can be expressed in vitro, on cells or be present in extracts. Association ($K_a$) and dissociation ($K_d$) constants can be measured using surface plasmon resonance (SPR) (Rich and Myszka, *Curr. Opin. Biotechnol.* 11:54 (2000); Englebienne, *Analyst.* 123: 1599 (1998)). SPR methods for real time detection and monitoring of protein binding rates are known and are commercially available and can be used to determine dissociation ($K_d$) constants (BiaCore 2000, Biacore AB, Upsala, Sweden; and Malmqvist, *Biochem. Soc. Trans.* 27:335 (1999)).

As used herein, the term "contact" and grammatical variations thereof means a physical or functional interaction between one entity and one or more other entities. An example of physical contact is a direct or indirect binding, such as between a LIGHT inhibitor and a target or receptor. An example of a functional interaction is where an intermediate facilitates or mediates a change in activity of one entity by another entity, such as a signaling pathway where molecules within the pathway functionally interact but need not physically contact each other. In the methods, contact can occur in solution, in solid phase, in vitro, ex vivo or in vivo (i.e., in a subject).

In accordance with the invention, there are provided methods in solution, in solid phase, in vitro, ex vivo or in vivo (i.e., in a subject). In one embodiment, a method includes contacting or administering to a subject, e.g. a subject in need thereof, an amount of a LIGHT inhibitor to treat the subject. In one particular aspect, an amount of LIGHT inhibitor contacted with or administered to the subject is sufficient to reduce or inhibit lung or airway inflammation. In another particular aspect, an amount of LIGHT inhibitor contacted with or administered to the subject is sufficient to treat asthma. In a further aspect, an amount of LIGHT inhibitor is administered to a subject sufficient to treat a respiratory, interstitial, or pulmonary disease or disorder, or fibrotic disease or disorder. In a still further aspect, an amount of LIGHT inhibitor is administered to a subject whom has previously experienced an asthmatic episode or airway-constriction or obstruction, or is in need of airway-dilation, sufficient to inhibit or reduce airway-constriction or obstruction, or to increase, stimulate or improve airway-dilation.

As used herein, the term "associated with," when used in reference to the relationship between a symptom and a condition, disorder or disease, means that the symptom is caused by the referenced condition, disorder or disease, or is a secondary effect of the referenced condition, disorder or disease. A symptom that is present in a subject may therefore be the direct result of or caused by the referenced condition, or may be due at least in part to the subject reacting or responding to the referenced condition, disorder or disease, e.g., a secondary effect. For example, symptoms that occur during an asthmatic or allergic episode are due in part to hypersensitivity or an aberrant response of the immune system of the subject to the antigen/allergen.

As used herein, the term "subject" includes animals, typically mammalian animals, such as but not limited to humans, non-human primates (apes, gibbons, chimpanzees, orangutans, macaques), domestic animals (dogs and cats), farm animals (horses, cows, goats, sheep, pigs), and experimental animals (mouse, rat, rabbit, guinea pig). Subjects include animal disease models (e.g., asthma, allergy). Subjects include naturally occurring or non-naturally occurring mutated or non-human genetically engineered (e.g., transgenic or knockout) animals. Subjects further include animals having or at risk of having a chronic or acute condition, disorder or disease.

Conditions, disorders and diseases treatable in accordance with the invention include, for example, chronic or acute inflammatory conditions, disorders and diseases, allergies, allergic conditions, disorders and diseases. An "inflammatory" condition, disorder or disease refers to one or more physiological responses that characterize or constitute inflammation. An "allergy" or "allergic condition," as used herein refers to a hypersensitivity to a substance (e.g., an allergen). Allergic conditions, disorders and diseases include but are not limited to allergic asthma, hayfever (seasonal rhinitis), allergic rhinitis, allergic conjunctivitis, eczema, urticaria, food allergies, and other atopic conditions.

Inflammatory, allergic and non-allergic and conditions, disorders and diseases of the respiratory system, including airways and lung, include asthma, chronic obstructive pulmonary disease ("COPD"), granulomatus diseases of the lungs and lower airway passages, non-malignant proliferative disease of the lungs e.g., idiopathic pulmonary fibrosis, hypersensitivity pneumonitis and bronchopulmonary dysplasia. Non-limiting examples of allergic conditions, disorders and diseases include, for example, extrinsic bronchial asthma; allergic rhinitis (AR); Onchocercal dermatitis; atopic dermatitis, drug reactions; nodules, eosinophilia, rheumatism, dermatitis, and swelling (NERDS); esophageal and gastro-intestinal (GI) allergies.

In accordance with the invention, there are provided methods of reducing progression, severity, frequency, duration, susceptibility or probability of inflammatory, allergic and non-allergic conditions, disorders and diseases of the respiratory system. In one embodiment, a method includes administering to a subject an amount of LIGHT inhibitor sufficient to reduce or decrease progression, severity, frequency, duration, susceptibility or probability of one or more adverse symptoms associated with inflammation in the respiratory tissue or organ.

In another embodiment, a method includes administering to a subject an amount of LIGHT inhibitor sufficient to reduce or decrease progression, severity, frequency, duration, susceptibility or probability of one or more adverse symptoms caused by or associated with asthma (allergic or non-allergic). In one aspect, the adverse symptom is selected from lung, airway or respiratory mucosum inflammation or tissue damage, shortness of breath, wheezing, coughing, chesttightness, chest pain, increased heart rate, runny nose, airway-constriction, decreased lung capacity, and an acute asthmatic episode. In another aspect, asthma is caused by or associated with exposure to an allergen or associated with exercise. In yet another aspect, the subject has been diagnosed as having asthma.

"Asthma" refers to an allergic or non-allergic condition, disorder or disease of the respiratory system that is episodic and characterized by inflammation with constriction, narrowing or obstruction of the airways. Allergic asthma is typically associated with increased reactivity of respiratory system (airways, lung, etc.) to an inhaled agent. Asthma is frequently, although not exclusively associated with atopic or allergic symptoms. Typically, a subject with asthma suffers from recurrent attacks of paroxysmal dyspnea (i.e., "reversible obstructive airway passage disease"), cough, shortness of breath with wheezing due to spasmodic contraction of the bronchi, sometimes referred to as "bronchospasm," chest pain, chest tightness, etc. While a plurality of such adverse symptoms typically occur in asthma, the existence of any one is usually adequate for diagnosis of asthma, and for treatment in accordance with the invention.

Asthmatic conditions include allergic asthma as well as bronchial allergy, which typically are provoked by a variety of factors including exercise such as vigorous exercise ("exercise-induced bronchospasm"), and irritant particles (allergens such as pollen, dust, venoms, cotton, dander, foods). Asthmatic conditions can be acute, chronic, mild, moderate or severe asthma (unstable asthma), nocturnal asthma or asthma associated with psychologic stress.

"Allergic rhinitis" is an allergic reaction of the nasal mucosa (upper airways), which includes hay fever (seasonal allergic rhinitis) and perennial rhinitis (non-seasonal allergic rhinitis) which are typically characterized by seasonal or perennial sneezing, rhinorrhea, nasal congestion, pruritis and eye itching, redness and tearing. "Non-allergic rhinitis" refers to eosinophilic non-allergic rhinitis, in subjects with negative skin tests, and subjects who have abnormal or undesirable numbers of eosinophils in their nasal secretions.

An "allergen" is a substance that can promote, stimulate or induce an allergic or asthmatic episode in a subject. Allergens include plant/tree pollens, insect venoms, animal dander, house dust mite, dust, fungal spores, latex, food and drugs (e.g., penicillin). Examples of particular allergens include proteins specific to the following genera: *Canis* (*Canis familiaris*); *Dermatophagoides* (e.g., *Dermatophagoides farinae*); *Felis* (*Felis domesticus*); *Ambrosia* (*Ambrosia artemiisfolia*); *Lolium* (e.g., *Lolium perenne* or *Lolium multiflorum*); *Cryptomeria* (*Cryptomeria japonica*); *Alternaria* (*Alternariaalternata*); *Alder; Alnus* (*Alnusgultinosa*); *Betula* (*Betulaverrucosa*); *Quercus* (*Quercus alba*); *Olea* (*Oleaeuropa*); *Artemisia* (*Artemisia vulgaris*); *Plantago* (e.g., *Plantagolanceolata*); *Parietaria* (e.g., *Parietariaofficinalisor Parietariajudaica*); *Blattella* (e.g., *Blattellagermanica*); *Apis* (e.g., *Apismultiflorum*); *Cupressus* (e.g., *Cupressussempervirens, Cupressusarizonica* and *Cupressusmacrocarpa*); *Juniperus* (e.g., *Juniperussabinoides, Juniperusvirginiana, Juniperuscommunis* and *Juniperusashei*); *Thuya* (e.g., *Thuyaorientalis*); *Chamaecyparis* (e.g., *Chamaecyparisobtusa*); *Periplaneta* (e.g., *Periplanetaamericana*); *Agropyron* (e.g., *Agropyronrepens*); *Secale* (e.g., *Secalecereale*); *Triticum* (e.g., *Triticumaestivum*); *Dactylis* (e.g., *Dactylisglomerata*); *Festuca* (e.g., *Festucaelatior*); *Poa* (e.g., *Poapratensisor Poacompressa*); *Avena* (e.g., *Avena sativa*); *Holcus* (e.g., *Holcuslanatus*); *Anthoxanthum* (e.g., *Anthoxanthumodoratum*); *Arrhenatherum* (e.g., *Arrhenatherumelatius*); *Agrostis* (e.g., *Agrostis alba*); *Phleum* (e.g., *Phleumpratense*); *Phalaris* (e.g., *Phalarisarundinacea*); *Paspalum* (e.g., *Paspalumnotatum*); *Sorghum* (e.g., *Sorghum halepensis*); and *Bromus* (e.g., *Bromus inermis*). Allergens also include peptides and polypeptides used in experimental animal models of allergy and asthma, including ovalbumin (OVA) and *Schistosoma mansoni* egg antigen.

A "respiratory disorder" or a "respiratory mucosum disorder" means a condition, disorder or disease related to a tissue or organ of the respiratory system. Examples include, but are not limited to, upper or lower airway inflammation, allergy (ies), breathing difficulty, cystic fibrosis (CF), allergic rhinitis (AR), Acute Respiratory Distress Syndrome (ARDS), pulmonary hypertension, lung inflammation, bronchitis, airway obstruction, airway constriction, airway narrowing, bronchoconstriction and inflammation associated with microbial or viral infections, such as influenza, picornaviridae (rhinoviruses such as human rhinovirus (HRV); enteroviruses (EV) such as polioviruses, coxsackieviruses and echoviruses) or severe acute respiratory syndrome (SARS). Additional non-limiting examples of respiratory disorders and respiratory mucosum disorders include apnea, asbestosis, atelectasis, berylliosis, bronchiectasis, bronchiolitis, bronchiolitis obliterans Organizing Pneumonia, Bronchitis, Bronchopulmonary Dysplasia, Common Cold, Cough, Empyema, Pleural Empyema, Pleural Epiglottitis, Hemoptysis, Hypertension, Kartagener Syndrome, Meconium Aspiration, Pleural Effusion, Pleurisy, Pneumonia, Pneumothorax, Respiratory Distress Syndrome, Respiratory Hypersensitivity, Respiratory Tract Infections, Rhinoscleroma, Scimitar Syndrome, Severe Acute Respiratory Syndrome (SARS), Silicosis, Tracheal Stenosis, and Whooping Cough.

Further non-limiting examples of interstitial and pulmonary disorders include Eosinophilic pleural effusions; Transient pulmonary eosinophilic infiltrates (Loffler); Histiocytosis; Chronic eosinophilic pneumonia; Hypersensitivity pneumonitis; Allergic bronchopulmonary aspergillosis; Sarcoidosis; Idiopathic pulmonary fibrosis; pulmonary edema; pulmonary embolism; pulmonary emphysema; Pulmonary Hyperventilation; Pulmonary Alveolar Proteinosis; Chronic Obstructive Pulmonary Disease; Interstitial Lung Diseases; and Topical eosinophilia.

The term "airway," as used herein, means a part of or the whole respiratory system of a subject that is exposed to air. "Airways" therefore include the upper and lower airway passages, within which are not limited to the trachea, bronchi, bronchioles, terminal and respiratory bronchioles, alveolar ducts and alveolar sacs. Airways include sinuses, nasal passages, nasal mucosum and nasal epithelium. The airway also includes, but is not limited to throat, larynx, tracheobronchial tree and tonsils.

Particular non-limiting examples of subjects include subjects having or at risk of having inflammation or lung or airways, an inflammatory or allergic condition, disorder or disease. Non-limiting examples of subjects further include subjects having or at risk of having an adverse or undesirable symptom associated with an inflammatory or allergic condition, disorder or disease, such as asthma. Such at risk subjects can be identified by a personal or family history, through genetic screening, tests appropriate for detection of increased risk, or exhibiting relevant symptoms indicating predisposition or susceptibility.

Subjects having or at risk of having an allergic condition, disorder or disease include subjects with an existing allergic condition or a known or a suspected predisposition towards developing a symptom associated with or caused by an allergic condition. Thus, the subject can have an active chronic allergic condition, disorder or disease, an acute allergic episode, or a latent allergic condition, disorder or disease. Certain allergic conditions, are associated with seasonal or geographical environmental factors. Thus, at risk subjects include those at risk from suffering from a condition based upon a prior personal or family history, and the season or physical location, but which the condition or a symptom associated with the condition may not presently manifest itself in the subject.

A subject having or at risk of having asthma refers to a subject suffering from an acute episode of asthma, either a new-onset or a recurrent episode, a subject with a prior history of one or more episodes of asthma, or a subject with a known or suspected predisposition towards developing asthma. A subject having asthma can have active asthma or can be asymptomatic and between acute asthma episodes. A subject having asthma can be suffering from recently acute asthmatic episode (e.g., within minutes or hours of episode onset). A subject having asthma can have a positive skin test, or exhibit one or more symptoms typically associated with acute or chronic asthma, for example, a symptom of allergic asthma. A subject having or at risk of having asthma may be or has been exposed to an allergen, for example, and is at increased risk of suffering from an asthmatic episode due to a predisposition or susceptibility towards an asthmatic episode upon re-exposure to the allergen. Subjects predisposed or susceptible to, exposed to or allergic to these or other allergens are at risk of having asthma and, therefore, are amenable to treatment in accordance with the invention.

At risk subjects also appropriate for treatment in accordance with the invention include subjects exposed to an allergen or are susceptible to having an allergic reaction, or infection or exposure by an agent that is associated with an allergy or allergic reaction. At risk subjects appropriate for treatment in accordance with the invention include subjects having a predisposition towards an allergic reaction, or infection or exposure to an agent that is associated with an allergy or allergic reaction due to a genetic or environmental risk factor. Methods of the invention include subjects contacted with or administered to a binding agent prophylactically.

In the methods of the invention in which a detectable result or beneficial effect is a desired outcome, such as a therapeutic benefit in a subject treated in accordance with the invention, compositions such as LIGHT inhibitors can be administered in sufficient or effective amounts. An "amount sufficient" or "amount effective" includes an amount that, in a given subject, can have a desired outcome or effect. The "amount sufficient" or "amount effective" can be an amount of a LIGHT inhibitor that provides, in single or multiple doses, alone or in combination with one or more other (second) compounds or agents (e.g., a drug), treatments or therapeutic regimens, a long or short term detectable response, a desired outcome or beneficial effect in a particular given subject of any measurable or detectable degree or duration (e.g., for minutes, hours, days, months, years, or cured).

An amount sufficient or an amount effective can but need not be provided in a single administration and can but need not be administered alone (i.e., without a second drug, agent, treatment or therapeutic regimen), or in combination with another compound, agent, treatment or therapeutic regimen. In addition, an amount sufficient or an amount effective need not be sufficient or effective if given in single or multiple doses without a second compound, agent, treatment or therapeutic regimen, since additional doses, amounts or duration above and beyond such doses, or additional drugs, agents, treatment or therapeutic regimens may be included in order to be effective or sufficient in a given subject. Further, an amount sufficient or an amount effective need not be effective in each and every subject, nor a majority of subjects in a given group or population. Thus, as some subjects may not benefit from such treatments an amount sufficient or an amount effective means sufficiency or effectiveness in a particular subject, not a group or the general population. As is typical for such methods, some subjects will exhibit a greater or less response to a method of the invention, including treatment/therapy.

Reducing, inhibiting decreasing, eliminating, delaying, halting or preventing a progression or worsening or an adverse symptom of the condition, disorder or disease is a satisfactory outcome. The dose amount, frequency or duration may be proportionally increased or reduced, as indicated by the status of the condition, disorder or disease being treated, or any adverse side effects of the treatment or therapy. Dose amounts, frequencies or duration also considered sufficient and effective are those that result in a reduction of the use of another drug, agent, treatment or therapeutic regimen or protocol. For example, a LIGHT inhibitor is considered as having a beneficial or therapeutic effect if contact, administration or delivery in vivo results in the use of a lesser amount, frequency or duration of another drug, agent, treatment or therapeutic regimen or protocol to treat the condition, disorder or disease, or an adverse symptom thereof.

An "amount sufficient" or "amount effective" includes reducing, preventing, delaying or inhibiting onset, reducing, inhibiting, delaying, preventing or halting the progression or worsening of, reducing, relieving, alleviating the severity, frequency, duration, susceptibility or probability of one or more adverse or undesirable symptoms associated with the condition, disorder or disease of the subject. In addition, hastening a subject's recovery from one or more adverse or undesirable symptoms associated with the condition, disorder or disease is considered to be an amount sufficient or effective. Various beneficial effects and indicia of therapeutic benefit are as set forth herein and are known to the skilled artisan.

An "amount sufficient" or "amount effective," in the appropriate context, can refer to therapeutic or prophylactic amounts. Therapeutically or prophylactically sufficient or effective amounts mean an amount that, in a given subject, detectably improves the condition, disorder or disease, such as an inflammatory condition, disorder or disease, as assessed by one or more objective or subjective clinical endpoints appropriate for the condition, disorder or disease.

In accordance with the invention, there are provided methods which provide a beneficial effect, such as a therapeutic benefit, to a subject. In one embodiment, a method includes administering an amount of LIGHT inhibitor sufficient to provide a therapeutic benefit or beneficial effect to a subject. In one aspect, a method reduces or inhibits probability, susceptibility, severity, frequency, duration or prevents lung or airway inflammation in the subject. In another aspect, a method reduces the probability, susceptibility, severity, frequency, duration or prevents an asthmatic episode (e.g., associated with allergic or non-allergic asthma) in the subject. In an additional aspect, a method reduces or inhibits probability, susceptibility, severity, frequency, duration or prevents a symptom caused by or associated with a respiratory, interstitial or pulmonary disease or disorder. In a further aspect, a method increases, stimulates, enhances, induces or promotes airway-dilation in the subject. In still another aspect, a method reduces the probability, susceptibility, severity, frequency, duration or prevents or eliminates airway-constriction the subject. In a yet further aspect, a method is sufficient to reduce progression, severity, frequency, duration, susceptibility, probability, halt, eliminate or prevent one or more adverse physiological or psychological symptoms associated with asthma (allergic or non-allergic).

Sufficiency or effectiveness of a particular treatment can be ascertained by various clinical indicia and endpoints. For example, in order to ascertain an improvement in asthma, an increase in airway dilation, lung function or a reduction in airway constriction, obstruction or narrowing, progression, severity, duration, frequency, susceptibility or probability of one or more symptoms of asthma. An "amount sufficient" or "amount effective" to treat asthma is therefore an amount that provides an objective or subjective reduction or improvement in progression, severity, frequency, susceptibility or probability of lung or airway inflammation, lung or airway tissue damage, shortness of breath, wheezing, coughing, chest-tightness, chest pain, increased heart rate, runny nose, airway or broncho-constriction, -obstruction or narrowing, decreased lung capacity, acute asthmatic episodes, nighttime awakenings, etc. Thus, a reduction, decrease, inhibition, delay, halt, prevention or elimination of one or more adverse symptoms (e.g., shortness of breath, wheezing, coughing, chest-tightness, chest pain, increased heart rate, runny nose, acute asthmatic episodes, nighttime awakenings, etc.) can be used as a measure of sufficiency or effectiveness.

A method to determine an improvement in lung or pulmonary function is to measure the forced expiratory volume in one second ($FEV_1$) an increase of which indicates an improvement. Spirometry is a test which measures the amount and rate at which air can pass through airways. Airway narrowing due to inflammation restricts air flow through the airways, which is detected by changed spirometry values. Exercise challenge and methacholine inhalation tests are also used to evaluate airway narrowing or constriction. Yet another method to determine an improvement is to measure serum IgE in a subject. A reduction in serum or bronchoalveolar lavage (BAL) fluid IgE is an objective measure of treatment efficacy. Various additional methods are known to the skilled artisan for detecting improvement in lung or pulmonary function.

An "amount sufficient" or "amount effective" also includes an amount that, when used in combination with another binding agent, drug, or treatment or therapeutic regimen, reduces the dosage frequency, dosage amount, or an adverse symptom or side effect of the other binding agent, drug or treatment or therapeutic regimen, or eliminates the need for the other binding agent, drug or treatment or therapeutic regimen. For example, an "amount sufficient" or "amount effective" of a LIGHT inhibitor could result in a reduction in the dosage frequency or dosage amount of a steroid, antihistamine, beta adrenergic agonist, anticholinergic, methylxanthine, anti-IgE, anti-leukotriene, anti-beta2 integrin, anti-CCR3 antagonist, or anti-selectin required to achieve the same clinical endpoint.

The terms "treat," "therapy" and grammatical variations thereof when used in reference to a method means the method provides an objective or subjective (perceived) improvement in a subjects' condition, disorder or disease, or an adverse symptom associated with the condition, disorder or disease. Non-limiting examples of an improvement can therefore reduce or decrease the probability, susceptibility or likelihood that the subject so treated will manifest one or more symptoms of the condition, disorder or disease. Additional symptoms and physiological or psychological responses caused by or associated with conditions, disorders or diseases associated with, for example, lung and airway inflammation, asthma and a respiratory, interstitial or pulmonary disease or disorder are set forth herein and known in the art and, therefore, improvements in these and other adverse symptoms or physiological or psychological responses can also be included in the methods of the invention.

Methods of the invention therefore include providing a detectable or measurable beneficial effect or therapeutic benefit to a subject, or any objective or subjective transient or temporary, or longer-term improvement (e.g., cure) in the condition. Thus, a satisfactory clinical endpoint is achieved when there is an incremental improvement in the subjects condition or a partial reduction in the severity, frequency, duration or progression of one or more associated adverse symptoms or complications or inhibition, reduction, elimination, prevention or reversal of one or more of the physiological, biochemical or cellular manifestations or characteristics of the condition, disorder or disease. A therapeutic benefit or improvement ("ameliorate" is used synonymously) therefore need not be complete ablation of any or all adverse symptoms or complications associated with the condition, disorder or disease but is any measurable or detectable objectively or subjectively meaningful improvement in the condition, disorder or disease. For example, inhibiting a worsening or progression of the condition, disorder or disease, or an associated symptom (e.g., slowing or stabilizing one or more symptoms, complications or physiological or psychological effects or responses), even if only for a few days, weeks or months, even if complete ablation of the condition, disorder or disease, or an associated adverse symptom is not achieved is considered to be beneficial effect.

Prophylactic methods are included. "Prophylaxis" and grammatical variations thereof mean a method in accordance with the invention in which contact, administration or in vivo delivery to a subject is prior to manifestation or onset of a condition, disorder or disease (or an associated symptom or physiological or psychological response), such that it can eliminate, prevent, inhibit, decrease or reduce the probability, susceptibility, onset or frequency of having a condition, disorder or disease, or an associated symptom. Target subject's for prophylaxis can be one of increased risk (probability or susceptibility) of contracting the condition, disorder or disease, or an associated symptom, or recurrence of a previously diagnosed condition, disorder or disease, or an associated symptom, as set forth herein.

Any compound or agent (e.g., drug), therapy or treatment having a beneficial, additive, synergistic or complementary activity or effect (beneficial or therapeutic) can be used in combination with a binding agent in accordance with the invention. A "second compound" or "second agent" refers to any compound or agent (e.g., drug) that is not the first compound or agent of the recited composition, e.g., if a first drug or agent is a particular LIGHT inhibitor, then a second drug or agent is different from the first LIGHT inhibitor. The second compound or agent can but need not be selective, for example, for binding to LIGHT, HVEM or LTβR.

In accordance with the invention there are provided methods in which a second compound or agent (e.g., drug) is administered to the subject. In one embodiment, a second compound or agent (e.g., drug) is administered to the subject prior to, with or following contacting or administering a LIGHT inhibitor.

Methods of the invention therefore include combination therapies and treatments. Examples of such combination therapies include separate or pooled compounds or LIGHT inhibitors (e.g., pooled antagonists, compounds or agents). Accordingly, combination compositions, therapies and treatments are provided, as well as methods of using such combinations, therapies and treatments in conjunction with the methods of the invention. Contact, administration or in vivo delivery of a compound or agent, such as a binding agent, or practice of a therapy or treatment, can occur prior to, in conjunction with or following a method or method step of the invention, e.g., prior to, in conjunction or following administering a LIGHT inhibitor.

Non-limiting examples of functional classes of compounds and agents useful as a second compound or agent (e.g., drug) include anti-inflammatory, anti-asthmatic, airway dilators (e.g., xanthine drugs such as methylxanthines, which are broncho-dilators) and anti-allergy drugs. Additional non-limiting examples of compounds and agents useful for employing in the invention, for example to treat an allergic condition, disorder or disease (e.g., asthma, allergic rhinitis) include hormones, such as steroids (e.g., glucocorticoids); antihistamines; beta adrenergic agonists; anticholinergics; methylxanthines; anti-IgE; anti-leukotrienes; anti-beta2 integrins; anti-alpha-4 integrins; H1-receptor antagonists; anti-CCR3 antagonists; and anti-selectins.

Specific non-limiting examples of glucocorticoids include dexamethasone, triamcinolone acetonide (AZMACORT®), beclomethasone, dipropionate (VANCERIL®), flunisolide (AEROBID®), fluticasone propionate (FLOVENT®), prednisone, methylprednisolone and mometasonefuroate (ASMANEX®, TWISTHALER®). Specific non-limiting examples of antihistamines include chlorcyclizine, chlorpheniramine, triprolidine (ACTIFED®), diphenhydramine hydrochloride (BENADRYL®), fexofenadine hydrochloride (ALLEGRA®), hydroxyzine hydrochloride (ATARAX®), loratadine (CLARITIN®), promethazine hydrochloride (PHENERGAN®), pyrilamine; and anti-IgE omalizumab (XOLAIR®). Specific non-limiting example of beta adrenergic agonists include albuterol (VENTOLIN®; PROVENTIL®), Xopenex®, (S)-isomer subtracted from racemic albuterol (Sepracor Inc.), pirbuterol, epinephrine, racepinephrine, adrenaline, isoproterenol, salmeterol (Serevent®), metaproterenol (ALUPENT®), bitolterol (Tornalate®), fenoterol (BEROTEC®), formoterol (Foradil®), isoetharine, procaterol, β2-adrenoceptor and terbutaline (BRETHINE®, LAMISIL®). A specific non-limiting example of an anticholinergic (cholinergic receptor antagonist) includes ipratropium bromide (ATROVENT®) and tiotropium. Specific non-limiting examples of methylxanthines include theophylline, aminophylline, theobromine, cromolyn (Intal®) and nedocromil (Fisons). A specific non-limiting example of an anti-IgE is omalizumab (XOLAIR®). Specific non-limiting examples of anti-leukotrienes (leukotriene inhibitors) include cysteinyl-leukotriene (Cys-LT), Singulair® and Accolate®.

Anti-inflammatory agents useful for employing in the methods include cytokines and chemokines. Particular non-limiting examples of cytokines include anti-inflammatory cytokines such as IL-4 and IL-10. Anti-cytokines and anti-chemokines, such as antibodies that bind to pro-inflammatory cytokines, TNFα, IFNγ, IL-1, IL-2, IL-6, etc., as well as anti-Th2 cytokines such as IL-5, IL-13, etc., can be employed in the methods.

Additional functional classes of compounds and agents useful as a second compound or agent (e.g., drug) include selective or non-selective potassium channel activators (bronchodilatators); muscarinic M3 receptor antagonists; M2 receptor agonists; opioid receptor agonists (inhibit release of sensory neuropeptides); H3-receptor agonists (inhibit acetylcholine release); phospholipase A2 inhibitors; 5-lipoxygenase inhibitors; 5-lipoxygenase activating protein (FLAP) inhibitors; phosphodiesterase inhibitors; immunomodulating agents (Ciclosporine); antibody against adhesion molecules; and antagonists of tachykinins (e.g., Substance P or neurokinin).

Compositions including LIGHT inhibitors can be included in a pharmaceutically acceptable carrier (excipient, diluent, vehicle or filling agent) for administration to a subject. The terms "pharmaceutically acceptable" and "physiologically acceptable" mean a biologically acceptable formulation, gaseous, liquid or solid, or mixture thereof, which is suitable for one or more routes of administration, in vivo delivery or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Supplementary active compounds (e.g., preservatives, antioxidants, antimicrobial agents including biocides and biostats such as antibacterial, antiviral and antifungal agents) can also be incorporated into the compositions. Pharmaceutical compositions may therefore include preservatives, antioxidants and antimicrobial agents.

Preservatives can be used to inhibit microbial growth or increase stability of the active ingredient thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

An antimicrobial agent or compound directly or indirectly inhibits, reduces, delays, halts, eliminates, arrests, suppresses or prevents contamination by or growth, infectivity, replication, proliferation, reproduction, of a pathogenic or non-pathogenic microbial organism. Classes of antimicrobials include, antibacterial, antiviral, antifungal and antiparasitics. Antimicrobials include agents and compounds that kill or destroy (-cidal) or inhibit (-static) contamination by or growth, infectivity, replication, proliferation, reproduction of the microbial organism.

Exemplary antibacterials (antibiotics) include penicillins (e.g., penicillin G, ampicillin, methicillin, oxacillin, and amoxicillin), cephalosporins (e.g., cefadroxil, ceforanid, cefotaxime, and ceftriaxone), tetracyclines (e.g., doxycycline, chlortetracycline, minocycline, and tetracycline), aminoglycosides (e.g., amikacin, gentamycin, kanamycin, neomycin, streptomycin, netilmicin, paromomycin and tobramycin), macrolides (e.g., azithromycin, clarithromycin, and erythromycin), fluoroquinolones (e.g., ciprofloxacin, lomefloxacin, and norfloxacin), and other antibiotics including chloramphenicol, clindamycin, cycloserine, isoniazid, rifampin, vancomycin, aztreonam, clavulanic acid, imipenem, polymyxin, bacitracin, amphotericin and nystatin.

Particular non-limiting classes of anti-virals include reverse transcriptase inhibitors; protease inhibitors; thymidine kinase inhibitors; sugar or glycoprotein synthesis inhibitors; structural protein synthesis inhibitors; nucleoside analogues; and viral maturation inhibitors. Specific non-limiting examples of anti-virals include nevirapine, delavirdine, efavirenz, saquinavir, ritonavir, indinavir, nelfinavir, amprenavir, zidovudine (AZT), stavudine (d4T), lamivudine (3TC), didanosine (DDI), zalcitabine (ddC), abacavir, acyclovir, penciclovir, valacyclovir, ganciclovir, 1,-D-ribofuranosyl-1,2,4-triazole-3 carboxamide, 9->2-hydroxy-ethoxy methylguanine, adamantanamine, 5-iodo-2'-deoxyuridine, trifluorothymidine, interferon and adenine arabinoside.

Exemplary antifungals include agents such as benzoic acid, undecylenicalkanolamide, ciclopiroxolamine, polyenes, imidazoles, allylamine, thicarbamates, amphotericin B, butylparaben, clindamycin, econaxole, amrolfine, butenafine, naftifine, terbinafine, ketoconazole, elubiol, econazole, econaxole, itraconazole, isoconazole, miconazole, sulconazole, clotrimazole, enilconazole, oxiconazole, tioconazole, terconazole, butoconazole, thiabendazole, voriconazole, saperconazole, sertaconazole, fenticonazole, posaconazole, bifonazole, fluconazole, flutrimazole, nystatin, pimaricin, amphotericin B, flucytosine, natamycin, tolnaftate, mafenide, dapsone, caspofungin, actofunicone, griseofulvin, potassium iodide, Gentian Violet, ciclopirox, ciclopiroxolamine, haloprogin, ketoconazole, undecylenate, silver sulfadiazine, undecylenic acid, undecylenicalkanolamide and Carbol-Fuchsin.

The pH can be adjusted by use or addition of pharmacologically acceptable acids or bases. Examples of inorganic acids include: hydrochloric acid, hydrobromic acid, nitric acid, sulfuric acid, and/or phosphoric acid. Examples of organic acids are: ascorbic acid, citric acid, malic acid, tartaric acid, maleic acid, succinic acid, fumaric acid, acetic acid, formic acid and/or propionic acid, etc. Acids which form an acid addition salt with the active ingredient may also be used. Examples of bases include alkali metal hydroxides and alkali metal carbonates. If such bases are used, the resulting salts which are contained in the pharmaceutical formulation, are typically compatible with the acid. If desired, mixtures of acids or bases may also be used.

Pharmaceutical compositions can optionally be formulated to be compatible with a particular route of administration. Thus, pharmaceutical compositions include carriers (excipients, diluents, vehicles or filling agents) suitable for administration by various routes and delivery to targets, locally, regionally or systemically.

Exemplary routes of administration for contact or in vivo delivery which a composition can optionally be formulated include respiratory system (nasal, inhalation, respiration, intubation, intrapulmonary instillation), oral, buccal, intrapulmonary, intrauterine, intradermal, topical, dermal, parenteral, sublingual, subcutaneous, intravascular, intrathecal, intraarticular, intracavity, transdermal, iontophoretic, intraocular, ophthalmic, optical, intravenous, intramuscular, intraglandular, intraorgan, intralymphatic.

Nasal and instillation formulations typically include aqueous solutions of active ingredient (compounds or agents) optionally with one or more preservative or isotonic agents. Such formulations are typically adjusted to a pH and isotonic state compatible with nasal mucous membranes. A solvent may include only water, or it may be a mixture of water and one or more other components (e.g., ethanol). Typically, the maximum ethanol is up to about 70-75%% by volume. The remaining volume may consist of water or one or more other solvents in various proportions.

Formulations that include respirable or inhalable liquid or solid particles of the active ingredient (e.g., compound, binding agent) can have particles of a size sufficiently small to pass through the mouth and larynx upon inhalation and continue into the airways of the lungs (e.g., bronchi and alveoli). Particles typically range in size from about 0.05, about 0.1, about 0.5, about 1, about 2 to about 4, about 6, about 8, about 10 microns in diameter. Particles of non-respirable size can be included in an aerosol or spray to deposit in the throat. For nasal administration or intrapulmonary instillation, a particle size in the range of about 8, about 10, about 20, about 25 to about 35, about 50, about 100, about 150, about 250, about 500 pm (diameter) is typical for retention in nasal cavity or for instillation into lung.

Formulations suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, or creams as generally known in the art. For contact with skin, pharmaceutical compositions typically include ointments, creams, lotions, pastes, gels, sprays, aerosols, or oils. Carriers which may be used include Vaseline, lanolin, polyethylene glycols, alcohols, transdermal enhancers, and combinations thereof.

Compounds including LIGHT inhibitors, either alone or in combination with a pharmaceutically acceptable carrier, second compound, drug, etc. can be administered into the respiratory system of a subject by inhalation, respiration, intubation, or intrapulmonary instillation (into the lungs), for example. Respiratory administration can be achieved using an aerosol or spray of a gas, liquid or powdered nasal, intrapulmonary, respirable or inhalable in a particle form. The particles include the compound or binding agent, and optionally any other component (e.g., second compound), and are administered or delivered to the subject by inhalation, by nasal administration or instillation into the airways or the lung.

Administration to airways can be accomplished using an article of manufacture, such as container with or without an aerosol. Liquid formulations may be squirted into the respiratory system (e.g., nose) and the lung from a container by pressure or using an aerosol propellant or a spray device or delivery system. Administration can be passive or it can be assisted by a pressurized delivery system or device. An aerosol, delivery system or device can include a pressurized container containing liquid, gas or dry powder.

An "aerosol formulation" refers to a preparation that includes droplets or particles of active ingredient (e.g., compound, binding agent) suitable for delivery to respiratory system (e.g., lung, airway, nasal and sinus epithelium). The aerosol formulation can include a sufficient or effective amount of a compound or agent and a pharmaceutically acceptable carrier, optionally a propellant, in a container or aerosol or spray device or delivery system. Aerosol formulations can deliver high concentrations into airways with relatively low systemic absorption, and include for example nasal sprays, inhalation solutions, inhalation suspensions, and inhalation sprays. Nasal sprays typically contain active ingredient dissolved or suspended in solution or in an excipient, in nonpressurized dispensers that deliver a metered dose of the ingredient.

For aerosol delivery, pH of the formulation is typically between 5.0 and 7.0. If the aerosol is too acidic or basic, it can cause bronchospasm and cough. The tolerized pH range is relative and depends on a patient's tolerance: some patients tolerate a mildly acidic aerosol, which in others will cause bronchospasm. Typically, an aerosol formulation having a pH less than 4.5 induces bronchospasm.

Compositions including compounds and binding agents can be formulated in a dry powder for delivery into the endobronchial space. Dry powder formulations provide stability, high volume delivery per puff, and low susceptibility to microbial growth. Dry powder formulations typically are stable at ambient temperature, and have a physiologically acceptable pH of 4.0-7.5. Dry powder formulations are convenient because they do not require any further handling, such as dilution, prior to administration. Depending on delivery device efficiency, effective dry powder dosage levels typically fall in the range of about 10 to about 100 mg. Dry powder formulations can be used directly in metered dose or dry powder inhalers.

Aerosol and spray delivery systems and devices, also referred to as "aerosol generators" and "spray generators" are known in the art and include metered dose inhalers (MDI), nebulizers (ultrasonic, electronic and other nebulizers), nasal sprayers and dry powder inhalers.

MDIs typically include an actuator, a metering valve, and a container that holds a suspension or solution, propellant, and surfactant (e.g., oleic acid, sorbitan trioleate, lecithin). The container may be pressurized or not, but typically it is either squeezed to dispense the ingredient, or has an actuator connected to a metering valve so that activation of the actuator causes a predetermined amount to be dispensed from the container in the form of an aerosol, which is inhaled by the subject. MDIs typically use liquid propellant. Typically, metered-dose aerosol inhalers create droplets that are 15 to 30 microns in diameter. Currently, MDI technology is optimized to deliver masses of 1 microgram to 10 mg of a therapeutic.

Nebulizers, also referred to as atomizers, are devices that turn medication into a fine mist inhalable by a subject through a face mask that covers the mouth and nose. Nebulizers provide small droplets and high mass output which can be delivered to upper and lower respiratory airways. Typically, nebulizers create droplets down to about 1 micron in diameter. Doses administered by nebulizers are typically larger than doses administered by MDIs.

Nebulizers include air-jet and ultrasonic nebulizers, in fluid connection with a reservoir containing disposed therein a solution or suspension of active ingredient. Nebulizers (airjet, ultrasonic or electronic) are typically used for acute care of nonambulatory patients and in infants and children. Airjet nebulizers are relatively large but considered portable because of the availability of small compressed air pumps. Ultrasonic and electronic nebulizers are typically more portable because they usually do not require a source of compressed air. An example of an airjet nebulizer is theNE-C25 CompAir XLT Compressor Nebulizer System(Omron® Healthcare). Examples of ultrasonic nebulizers include the Zewa Portable Ultrasonic Nebulizer (Zewa, Inc.); the Mabis-Mist II Ultrasonic Nebulizer (Mabis Healthcare, Inc.); and the MICROAir Ultrasonic Nebulizer (Omron® Healthcare). An example of an electronic nebulizer is the Micro-Air® Electronic Nebulizer with V.M.T. (Omron® Healthcare). Modified nebulizers can have the addition of a one-way flow valve (e.g., Pari LC Plus™, Pari Respiratory Equipment, Inc.), which delivers up to 20% more drug than unmodified nebulizers.

Components of the nebulizer are typically made of a material suitable for their intended function. The housing of the nebulizer and, if the function allows, other parts can be made of plastic (PVC, Polycarbonate, polystyrene, polypropylene, polybutylene, etc.). Plastic can be formed by injection molding. For medical applications, physiologically acceptable materials are used.

Dry-powder inhalers (DPI) can be used to deliver the compounds or agents, either alone or in combination with a pharmaceutically acceptable carrier, second compound, etc. Dry powder inhalers deliver active ingredient to airways and lungs while the subject inhales through the device. DPIs typically do not contain propellants or any other ingredients, only the medication, but may optionally include other components. DPIs are typically breath-activated, but may involve air or gas pressure to assist delivery. For breath-activated DPIs, a subject need not coordinate breathing with the activation of the inhaler.

There are two major DPI design classes. The first is a device-metering design in which a reservoir of drug is stored within the device and the subject 'loads' a dose of the device into the inhalation chamber, and the inspiratory flow of the patient accelerates the powder out of the device and into the oral cavity. The second type of DPI may also employ an air source, a gas source, or electrostatics, in order to deliver the active ingredient. Non-limiting examples of DPIs include Spinhaler® (Rhone-Poulenc Rorer Pharmaceuticals, Collegeville, Pa.), Inhalator® (Boehringer Ingelheim, Ingelheim, Germany), Rotahaler® (GlaxoSmithKline), Turbulaler® (Astra Draco Pharmaceuticals, Lund, Sweden) and Accuhaler (GlaxoSmithKline).

An aerosol, delivery system or device can include a propellant. Exemplary propellants include chlorofluorocarbons (e.g., trichlorofluoromethane, dichlorodifluoromethane, dichlorotetrafluoromethane, CFC-11, CFC-12) and the non-d chlorofluorocarbons, HFC-134A and HFC-227. Suitable fluorocarbon (HFA) propellants are known in the art and include, for example, HFA134a (1,1,1,2-tetrafluoroethane), HFA227 (1,1,1,2,3,3,3-heptafluoro-n-propane) and mixtures of HFA134a and HFA227.

Pharmaceutical compositions and delivery systems appropriate for compositions and methods of the invention are known to the skilled artisan (see, e.g., *Remington: The Science and Practice of Pharmacy* (2003) 20$^{th}$ ed., Mack Publishing Co., Easton, Pa.; *Remington's Pharmaceutical Sciences* (1990) 18$^{th}$ ed., Mack Publishing Co., Easton, Pa.; *The Merck Index* (1996) 12$^{th}$ ed., Merck Publishing Group, Whitehouse, N.J.; *Pharmaceutical Principles of Solid Dosage Forms* (1993), Technonic Publishing Co., Inc., Lancaster, Pa.; Ansel and *Stoklosa, Pharmaceutical Calculations* (2001) 11$^{th}$ ed., Lippincott Williams & Wilkins, Baltimore, Md.; and Poznansky et al., *Drug Delivery Systems* (1980), R. L. Juliano, ed., Oxford, N.Y., pp. 253-315)

LIGHT inhibitors and pharmaceutical compositions thereof can be packaged in unit dosage form (capsules, troches, cachets, lozenges, or tablets) for ease of administration and uniformity of dosage. "Unit dosage form" as used herein refers to physically discrete units suited as dosages for treatment or therapy. Each unit contains a predetermined quantity of agent in association with the pharmaceutical carrier (excipient, diluent, vehicle or filling agent) which, when administered in one or more doses, is calculated to produce a desired beneficial effect. Unit dosage forms also include, for example, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Unit dosage forms further include compositions for transdermal administration, such as "patches" adapted to remain in contact with the epidermis of the intended recipient for an extended or brief period of time. The individual unit dosage forms can be included in multi-dose kits or containers.

Dose amounts, frequency and duration for binding agents, including LIGHT inhibitors, or pro-drugs therof, can be can be empirically determined in appropriate animal models. Dose amounts, frequency and duration can also be determined and optimized in human clinical trials.

The dosage amount can range from about 0.0001 mg/kg of subject body weight/day to about 1,000.0 mg/kg of subject body weight/day. Of course, doses can be more or less, as appropriate, for example, 0.00001 mg/kg of subject body weight to about 10,000.0 mg/kg of subject body weight, about 0.001 mg/kg, to about 1,000 mg/kg, about 0.01 mg/kg, to about 100 mg/kg, or about 0.1 mg/kg, to about 10 mg/kg of subject body weight over a given time period, e.g., 1, 2, 3, 4, 5 or more hours, days, weeks, months, years, in single bolus or in divided/metered doses.

As a non-limiting example, for treatment of lung or airway inflammation, or asthma (e.g., allergic or non-allergic asthma or rhinitis), a subject may be administered in single bolus or in divided/metered doses in the range of about 10 to 50,000 micrograms ("mcg")/day, 10 to 20,000 mcg/day, 10 to 10,000 mcg/day, 25-1,000 mcg/day, 25 to 400 mcg/day, 25-200 mcg/day, 25-100 mcg/day or 25-50 mcg/day, which can be adjusted to be greater or less according to the weight of the subject, e.g., per pound, kilogram, etc.

LIGHT inhibitors, combinations of LIGHT inhibitors and other actives and pharmaceutical formulations thereof can be administered to a subject at any frequency, as a single bolus or in divided/metered doses, one, two, three, four or more times over a given time period, e.g., per hour, day, week, month or year. Exemplary dosage frequencies for airway or lung conditions, disorders or diseases, such as asthma can vary, but are typically from 1-7 times, 1-5 times, 1-3 times, 2-times or once, daily, weekly or monthly, to reduce, inhibit, decrease, delay, prevent, halt or eliminate progression, severity, frequency, duration, or probability of one or more adverse symptoms of the conditions, disorders or diseases, as set forth herein or that would be apparent to one skilled in the art. Timing of contact, administration or in vivo delivery can be dictated by the condition, disorder or disease to be treated. For example, an amount can be administered to the subject substantially contemporaneously with, or within about 1-60 minutes or hours of the onset of a symptom associated with or caused by lung or airway inflammation, asthma (e.g., non-allergic asthma, allergic asthma, or an asthmatic episode) or airway-constriction, -narrowing or -obstruction, or a respiratory, interstitial or pulmonary disease or disorder.

Dosage amount, frequency or duration can be increased, if necessary, or reduced, for example, once control of the condition, disorder or disease is achieved, dose amounts, frequency or duration can be reduced. Other conditions, disorders or diseases of the airways and lungs can be similarly treated, dosing amount, frequency or duration reduced, when adequate control of the condition, disorder or disease is achieved.

Of course, the dosage amount, frequency and duration can vary depending upon the judgment of the skilled artisan which will consider various factors such as whether the treatment is prophylactic or therapeutic, the type or severity of the condition, disorder or disease, the associated symptom to be treated, the clinical endpoint(s) desired such as the type and duration of beneficial or therapeutic effect. Additional non-limiting factors to consider in determining appropriate dosage amounts, frequency, and duration include previous or simultaneous treatments, potential adverse systemic, regional or local side effects, the individual subject (e.g., general health, age, gender, race, bioavailability), condition of the subject such as other disorders or diseases present and other treatments or therapies that the subject has or is undergoing (e.g., medical history). The skilled artisan will appreciate the factors that may influence the dosage, frequency and duration required to provide an amount sufficient to provide a subject with a beneficial effect, such as a therapeutic benefit.

The invention provides kits including LIGHT inhibitors suitable for practicing the methods, treatment protocols or therapeutic regimes herein, and suitable packing material. In one embodiment, a kit includes a LIGHT inhibitor, and instructions for administering or using the LIGHT inhibitor. In another embodiment, a kit includes a LIGHT inhibitor, an article of manufacture for delivery of the LIGHT inhibitor to the target area, organ, tissue or system (e.g., lungs or airways), and instructions for administering the LIGHT inhibitor.

The term "packing material" refers to a physical structure housing a component of the kit. The material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to a ampule, tube or vial containing a kit component. Labels or inserts can additionally include a computer readable medium, such as a disk (e.g., floppy diskette, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein (e.g., the binding agent or pharmaceutical composition), dose amounts, clinical pharmacology of the active agent(s) including mechanism of action, pharmacokinetics and pharmacodynamics. Labels or inserts can include information identifying manufacturer information, lot numbers, and location and date of manufacture.

Labels or inserts can include information on a condition, disorder or disease for which a kit component may be used. Labels or inserts can include instructions for the clinician or subject for using one or more of the kit components in a method, or treatment protocol or therapeutic regimen. Instructions can include dosage amounts, frequency or duration, and instructions for practicing any of the methods, treatment protocols or therapeutic regimes described herein.

Labels or inserts can include information on any benefit that a component may provide, such as a therapeutic benefit. For example, a non-limiting examples of a benefit would be improved breathing or respiration, increased or improved airway dilation, etc. A benefit could also include a reduced need (amount, frequency or duration) for other medications, treatment protocols or therapeutic regimes that the subject may be using or have used for treatment of the condition, disorder or disease.

Labels or inserts can include information on potential adverse side effects, such as warnings to the subject or clinician regarding situations where it would not be appropriate to use a particular composition (e.g., a LIGHT inhibitor). For example, adverse side effects are generally more likely to occur at higher dose amounts, frequency or duration of the active agent and, therefore, instructions could include recommendations against higher dose amounts, frequency or duration. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities. Non-limiting examples of adverse side effects include, for example, hypersensitivity, rash, neurological effects such as tachycardia; palpitations; headache; tremor and nervousness.

In accordance with the invention, there are provided methods of identifying an agent that reduces or inhibits lung or airway inflammation, methods of identifying an agent for treating asthma and methods of identifying an agent for treating fibrosis. In one embodiment, a method includes administering a test inhibitor of LIGHT (p30 polypeptide) to a subject; and measuring lung or airway inflammation in the subject, wherein a reduction or inhibition of lung or airway inflammation identifies the test inhibitor as an agent that reduces or inhibits lung or airway inflammation. In another embodiment, a method includes administering a test inhibitor of LIGHT (p30 polypeptide) to a subject; and measuring a symptom of asthma in the subject, wherein a reduction or inhibition of a symptom of asthma identifies the test inhibitor as an agent for treating asthma. In a further embodiment, a method includes administering a test inhibitor of LIGHT (p30 polypeptide) to a subject; and measuring a symptom of fibrosis in the subject, wherein a reduction or inhibition of a symptom of fibrosis identifies the test inhibitor as an agent for treating fibrosis.

Unless otherwise defined, all technical and scientific terms used herein have the same meaning as commonly understood by one of ordinary skill in the art to which this invention relates. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "a LIGHT inhibitor" includes a plurality of LIGHT inhibitors; and reference to "a symptom" includes a plurality of symptoms (e.g., adverse or undesirable). Of course, this does not preclude limiting certain embodiments of the invention to specific LIGHT inhibitors or antagonists, particular symptoms, particular conditions, disorders or diseases, particular subjects, etc., using appropriate language.

As used herein, all numerical values or numerical ranges include integers within such ranges and fractions of the values or the integers within ranges unless the context clearly indicates otherwise. Thus, to illustrate, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 0-72 hrs, includes 1, 2, 3, 4, 5, 6, 7 hrs, etc., as well as 1, 2, 3, 4, 5, 6, 7 minutes, etc., and so forth. Reference to a range of doses, such as 0.1-1 ug/kg, 1-10 ug/kg, 10-25 ug/kg, 25-50 ug/kg, 50-100 ug/kg, 100-500 ug/kg, 500-1,000 ug/kg, 1-5 mg/kg, 5-10 mg/kg, 10-20 mg/kg, 20-50 mg/kg, 50-100 mg/kg, 100-250 mg/kg, 250-500 mg/kg, includes 0.11-0.9 ug/kg, 2-9 ug/kg, 11.5-24.5 ug/kg, 26-49 ug/kg, 55-90 ug/kg, 125-400 ug/kg, 750-800 ug/kg, 1.1-4.9 mg/kg, 6-9 mg/kg, 11.5-19.5 mg/kg, 21-49 mg/kg, 55-90 mg/kg, 125-200 mg/kg, 275.5-450.1 mg/kg, etc.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis disclosed herein. As an example, the invention includes embodiments in which specific subject matter disclosed herein is excluded from the embodiments. Thus, even though the invention is generally not expressed herein in terms of what the invention does not include, aspects that are not expressly included in the invention are nevertheless expressly or inherently disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example includes studies showing LIGHT plays a role in the development of chronic allergic lung inflammation and airway remodeling.

Wild type C57BL/6 and LIGHT-deficient (LIGHT-/-) mice were sensitized with 50 ug ovalbumin (OVA) with 0.5 mg alum intraperitoneally (i.p.) on days 0 and 12 followed by 20 ug OVA intranasal challenges on days 24, 26, 28 and then two times per week for 4 weeks. Percent of BAL eosinophils at 1 day and 3 days after last OVA challenge was determined. Results are shown in FIG. 1. BAL eosinophils are from 4 mice per group for each time point.

Another study was conducted using wild type C57BL/6 and LIGHT-deficient (LIGHT -/-) mice sensitized with 50 ug ovalbumin (OVA) with 0.5 mg alum intraperitoneally (i.p.) on days 0 and 12 followed by 20 ug intranasal OVA challenges on days 24, 26, 28 and then two times per week for 6 weeks. Lung sections were stained with trichrome to measure fibrosis, and for alpha-smooth muscle actin to measure development of smooth muscle mass, both features of airway remodeling; histographs are shown in FIG. 2A. The area of fibrosis or smooth muscle was quantified using image analysis with normalization for bronchial size, as shown in FIG. 2B. Results are means +/-SEM of 36-48 bronchial regions per group.

Figure 3:
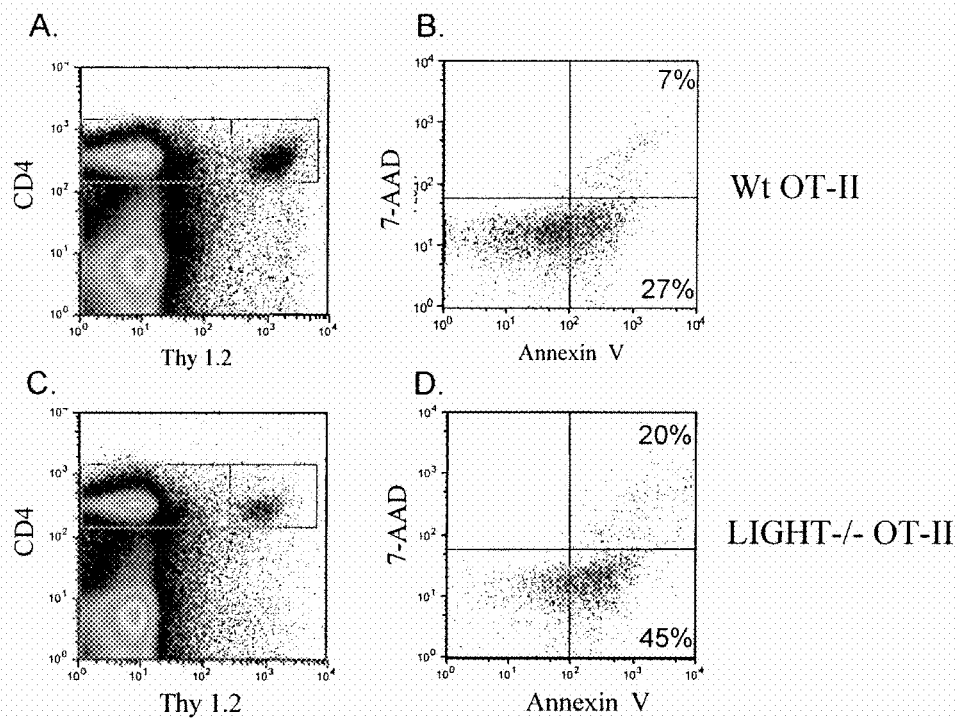
FIGS. 3A-3D show that LIGHT-deficient CD4 cells undergo extensive apoptosis after encountering antigen in vivo: Left (top and bottom) shows antigen-specific CD4 T cells (OT-II) visualized by staining for Thy1.2 and CD4; Right (top and bottom) shows the degree of apoptosis occurring within these CD4 T cell populations determined by co-staining for annexin V and 7-AAD after gating on Thy1.2+ cells. The percentages of early and late apoptotic cells are indicated.

Additionally naïve CD4 cells from wild-type (wt) or LIGHT-/- OT-II TCR transgenic mice were adoptively transferred into wt B6.PL recipients. Mice were immunized i.p. with OVA in Alum to generate Th2 cells. Transferred OT-II cells were visualized on day 8 by staining for Thy1.2 and CD4, as shown in FIG. 3A and FIG. 3C. The degree of apoptosis occurring within these populations was determined by co-staining for annexin V and 7-AAD after gating on Thy1.2+ cells, as shown in FIG. 3B and FIG. 3D. The percentages of early and late apoptotic cells are indicated. Data are representative of 4 mice per group.

As described above, when LIGHT-deficient mice were sensitized with ovalbumin (OVA) followed by repetitive intranasal OVA challenges for four to six weeks, they exhibited reduced eosinophilic lung inflammation (FIG. 1). Additionally, markedly reduced peribronchial fibrosis and smooth muscle mass was found in LIGHT-deficient mice. There was a 40-50% reduction in subepithelial fibrosis and smooth muscle mass, important pathologic remodeling features of chronic asthma (FIG. 2).

LIGHT may be directly acting in the lung to induce chronic asthmatic changes. A potential source of LIGHT in the inflamed lung are CD4+ T cells which are recovered at high levels in BAL specimens from human asthmatics.

To investigate the role of LIGHT on CD4 cells, LIGHT-deficient CD4 T cells were evaluated in adoptive recipients that were immunized with OVA. When OVA-reactive T cells were enumerated at the peak of the primary response (day 7), there was a strong reduction in their number (80-90%) when LIGHT was not expressed. As evidence that LIGHT controls the longevity and survival of T cells, staining for annexin V and 7-AAD in FIGS. 3B and 3D demonstrated that OVA-reactive CD4 cells displayed enhanced percentages undergoing apoptosis, a prelude to death, in the absence of LIGHT.

Example 2

This example includes studies demonstrating the requirement of LIGHT in lung inflammation by controlling T cells, in a system whereby T cells that could not express LIGHT were used to try to induce asthmatic lung inflammation. Naïve wild-type (wt) or LIGHT-/- OT-II CD4 T cells were activated in vitro for 3 days with anti-CD3 and anti-CD28 plus IL-4, IL-2, and anti-IFN-γ, and then recultured without further stimulation for 3 days. The resultant Th2 cells were transferred into naïve B6.PL recipients. Mice were exposed to aerosolized OVA or PBS and then rested for several weeks. Mice were then re-exposed to aerosolized OVA or PBS for 2 consecutive days. 1 day after the last challenge, lung and bronchial lavage samples were obtained. Lung histology, by H&E; sections from two individual OVA-challenged mice are shown in FIG. 4A. Total leukocyte and eosinophil counts by differential cytospin stain; and IL-5 and IL-13 expression by ELISA, were measured, results are shown in FIG. 4B. First set of data in each case, animals challenged with PBS. Second set, animals challenged with OVA. Data from individual mice are shown with 3 mice per group.

Figure 4:
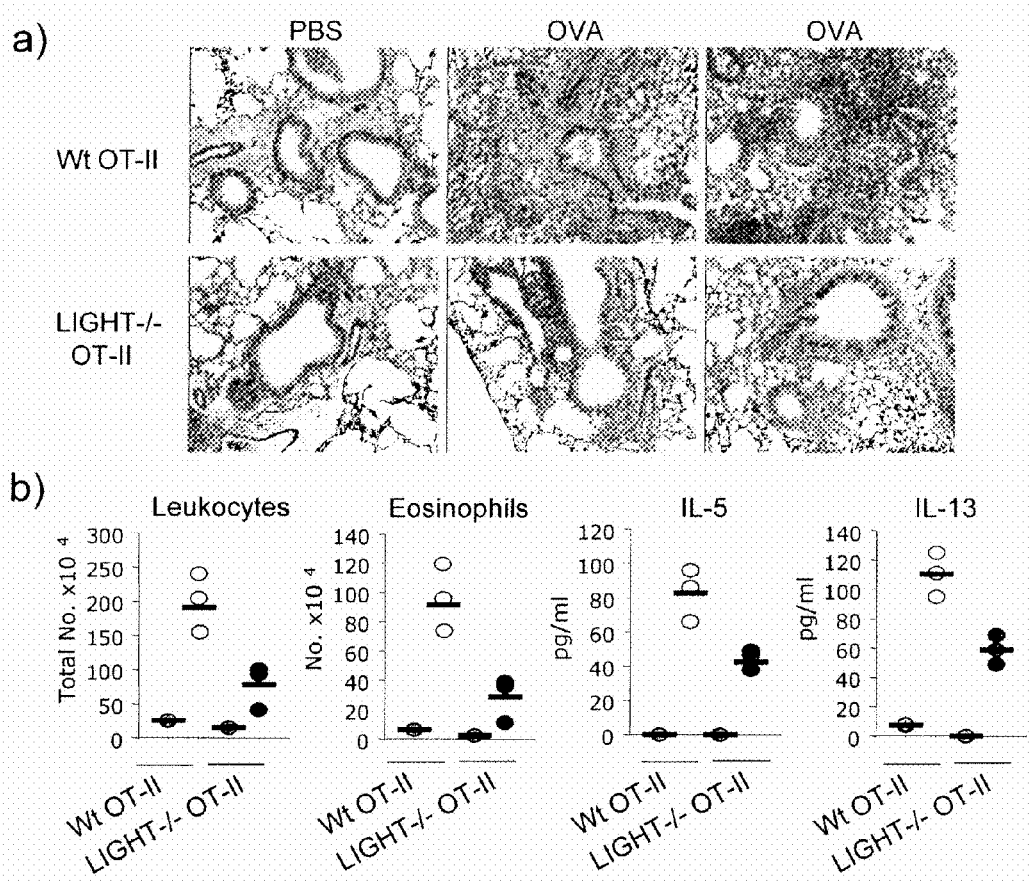
FIGS. 4A-4B show LIGHT-deficient CD4 T cells are defective in promoting asthmatic lung inflammation: A) lung histology, by H&E; sections from two individual antigen-challenged mice receiving wild-type or LIGHT-deficient Th2 (OT-II) cells; and B) total leukocyte and eosinophil counts by differential cytospin stain; and measurements of IL-5 and IL-13 expression by ELISA in bronchoalveolar samples. First set of data in each case, animals challenged with PBS. Second set, animals challenged with OVA.

In another study, using the experimental protocol in FIG. 4, the total number of wt OT-II (left two bars) and LIGHT-/-OT-II (right two bars) CD4 T cells accumulating after PBS or OVA challenge were enumerated in mediastinal lymph nodes and lung after staining for CD4 and Thy1.2 (FIG. 5). Data were average numbers from 3 mice per group.

In another study, naïve wild-type (Wt) or LIGHT-/- OT-II CD4 T cells were activated in vitro as in FIG. 4. The Th2 cells were adoptively transferred i.v. into naïve C57/BL6 WT hosts. Mice received 20 ug OVA intranasal challenges on day 1, 3, 5 and then chronic airway challenges two times per week for four weeks beginning one day after cell transfer and were sacrificed one day after last challenge. Percentages (left) and absolute numbers (right) of donor CD4 Th2 cells expressing OVA-specific TCR Vα2Vβ5 were determined in Bronchoalveolar lavage (BAL; FIG. 6A), Lung (FIG. 6B), and lung-draining lymph node (FIG. 6C). Samples were pooled from 3 mice in each group.

Transfer of primed Th2 cells into naïve wild-type recipients followed by administration of inhaled antigen showed that lung inflammation was profoundly impaired when LIGHT was absent (FIG. 4). Inflammatory infiltrates in the lung were reduced based on histological examination (FIG. 4A), and the levels of Th2 cytokines and eosinophils present in bronchial lavages were reduced when LIGHT-deficient CD4 cells were used (FIG. 4B). The accumulation of LIGHT-deficient T cells in lungs and lung draining lymph nodes was substantially lower after airway challenge such that a 70-80% reduction in numbers was observed compared to animals receiving control T cells that expressed LIGHT (FIG. 5).

To evaluate how LIGHT controls Th2 cells after chronic repetitive allergen challenges that may be more relevant to human asthma, LIGHT deficient and wild type CD4 cells were adoptively transferred into wt mice followed by 11 intranasal challenges over 5 weeks. Strikingly, LIGHT-deficient T cells completely failed to accumulate in the lung, bronchoalveolar lavage (BAL), and lung draining lymph nodes (FIG. 6). The data show that LIGHT is essential for controlling T cells in hosts that are repetitively challenged with antigen in the lung over a long period of time.

Example 3

This example includes shows reduction of lung inflammation after treatment with lymphotoxin beta receptor fusion protein during chronic allergen challenge via the airways.

Wild type C57BL/6 mice were sensitized with 50 ug ovalbumin (OVA) with 0.5 mg alum intraperitoneally (i.p.) on days 0 and 12 followed by 20 ug intranasal OVA challenges on days 24, 26, 28. Mice were then intranasally challenged two times per week for four more weeks with OVA, and lymphotoxin beta receptor Ig fusion protein (LTβR-Ig) was administered i.p. (50 ug) twice per week starting one day before these OVA challenges. FIG. 7A shows total cell infiltrate and eosinophils in BAL and FIG. 7B shows Total cell infiltrate and eosinophils in lungs. BAL results from 6 mice per group +/- SEM and Lung cell results are from pooled lungs from 3 mice per group.

In order to test a therapeutic intervention in the model of chronic asthma, a fusion protein (as described above) which contains the lymphotoxin beta receptor (LTβR) attached to the constant region of human immunoglobulin IgG (LTβR-Ig) was administered to mice only after acute OVA-induced lung inflammation was established, and treatment continued for four weeks during repetitive antigen challenges via the airways. Compared with mice that received control IgG there were reduced BAL leukocytes and eosinophils, along with markedly decreased total lung cells and eosinophils (FIG. 7). These results show that treatments targeting LIGHT can be efficacious in chronic asthma.

The data show that the TNFR superfamily member LIGHT is critical to the development of allergen induced airway remodeling and fibrosis. Disruption of the LIGHT pathways by targeting LIGHT therapeutically reduces lung inflammation. The foregoing data therefore indicate that treatment targeting LIGHT can be efficacious in asthma as well as other fibroproliferative diseases in the lung, and other organs.

What is claimed is:

1. A method for reducing or inhibiting lung airway remodeling or fibrosis in a subject with asthma, comprising administering a sufficient amount of an inhibitor of LIGHT (p30 polypeptide) comprising: a LTβR (lymphotoxin beta receptor) polypeptide subsequence, a soluble LTβR, a dominant-negative variant of LTβR, or a chimeric polypeptide comprising an LTβR polypeptide, LTβR polypeptide subsequence, soluble LTβR or dominant-negative variant of LTβR to the subject with asthma to reduce or inhibit lung airway remodeling or fibrosis.

2. A method for treating lung airway remodeling or fibrosis in a subject with asthma, comprising administering a sufficient amount of an inhibitor of LIGHT (p30 polypeptide) comprising: a LTβR (lymphotoxin beta receptor) polypeptide subsequence, a soluble LTβR, a dominant-negative variant of LTβR, or a chimeric polypeptide comprising an LTβR polypeptide, LTβR polypeptide subsequence, soluble LTβR or dominant-negative variant of LTβR to the subject with asthma to treat lung airway remodeling or fibrosis.

3. The method of claim 1, wherein the subject has allergic asthma.

4. A method for reducing or inhibiting lung airway remodeling or fibrosis in a subject with: Extrinsic bronchial asthma; Hypersensitivity pneumonitis; Allergic bronchopulmonaryaspergillosis; or Chronic eosinophilic pneumonia comprising administering a sufficient amount of an inhibitor of LIGHT (p30 polypeptide) comprising: a LTβR (lymphotoxin beta receptor) polypeptide subsequence, a soluble LTβR, a dominant-negative variant of LTβR, or a chimeric polypeptide comprising an LT βR polypeptide LTβR polypeptide subsequence soluble LTβR or dominant-negative variant of LTβR to the subject to treat lung airway remodeling or fibrosis.

5. A method for reducing or inhibiting lung airway remodeling or fibrosis in a subject with: Asbestosis, Bronchiolitis, Bronchitis, Silicosis, Sarcoidosis, Idiopathic pulmonary fibrosis, Chronic Obstructive Pulmonary Disease (COPD); Interstitial Lung Disease; or Cystic Fibrosis comprising administering a sufficient amount of an inhibitor of LIGHT (p30 polypeptide) comprising: a LTl3R (lymphotoxin beta receptor) polypeptide subsequence, a soluble LTβR, a dominant-negative variant of LTβR, or a chimeric polypeptide comprising an LTβR polypeptide, LTβR polypeptide subsequence, soluble LTβR or dominant-negative variant of LTβR to the subject to treat lung airway remodeling or fibrosis.

6. The method of claim 1, wherein the subject has non-allergic asthma.

7. The method of claim 1, 4 or 5, wherein the method reduces, decreases, inhibits, delays, eliminates or prevents the probability, severity, frequency, or duration of one or more symptoms associated with or caused by the lung airway remodeling or fibrosis.

8. The method of claim 1, 4 or 5, wherein one or more symptoms of the lung airway-remodeling or fibrosis is reduced, inhibited, abrogated, eliminated or reversed.

9. The method of claim 8, wherein the symptom comprises shortness of breath (dyspnea), wheezing, stridor, coughing, rapid breathing (tachypnea), prolonged expiration, runny nose, rhonchous lung, over-inflation of the chest or chest-tightness, decreased lung capacity, an acute asthmatic episode, or lung, airway or respiratory mucosum inflammation or tissue damage.

10. The method of claim 8, wherein the symptom comprises infiltration of eosinophils in lung, lung draining lymph nodes or airway, leukocyte infiltration of lung draining lymph nodes or airway, hyperplasia of mucus secreting epithelium, inflammatory lesion of lung, goblet cell hyperplasia, or increased Th2 cytokine production.

11. The method of claim 10, wherein the Th2 cytokine is an interleukin (IL).

12. The method of claim 11, wherein the interleukin (IL) is IL-4, IL-5, IL-9, IL-13, IL-16, IL-17 or IL-25.

13. The method of claim 1, 4 or 5, wherein the method reduces or inhibits progression, severity, frequency, duration or probability of a symptom of the lung airway remodeling or fibrosis.

14. The method of claim 1, wherein the lung airway remodeling or fibrosis is caused by an allergen.

15. The method of claim 1, 4 or 5, wherein the lung airway remodeling or fibrosis is chronic or acute.

16. The method of claim 1, 2, 4 or 5, wherein the subject is a mammal.

17. The method of claim 1, 2, 4 or 5, wherein the subject is a human.

18. The method of claim 1, 2, 4 or 5, wherein the method reduces or decreases undesirable or abnormal eosinophil migration, chemotaxis or generation.

19. The method of claim 1, 2, 4 or 5, wherein the LTβR polypeptide subsequence, soluble LTβR, dominant-negative variant of LTβR, or chimeric polypeptide comprising an LTβR polypeptide, LTβR polypeptide subsequence, soluble LTβR or dominant-negative variant of LTβR is administered via inhalation.

20. The method of claim 1, 2, 4 or 5, wherein the LTβR polypeptide subsequence, soluble LTZβR, dominant-negative variant of LTβR, or chimeric polypeptide comprising an LTβR polypeptide, LTβR polypeptide subsequence, soluble LTβR or dominant-negative variant of LTβR is formulated into an aerosol.

21. The method of claim 1, 2, 4 or 5, wherein the LTβR polypeptide subsequence, soluble LTβR, dominant-negative variant of LTβR, or chimeric polypeptide comprising an LTβR polypeptide, LTβR polypeptide subsequence, soluble LTβR or dominant-negative variant of LTβR is delivered to the lung airways.

\* \* \* \* \*

SEQUENCE LISTING

<160> NUMBER OF SEQ ID NOS: 3

<210> SEQ ID NO 1
<211> LENGTH: 240
<212> TYPE: PRT
<213> ORGANISM: Homo sapiens

<400> SEQUENCE: 1

```
Met Glu Glu Ser Val Val Arg Pro Ser Val Phe Val Val Asp Gly Gln
 1               5                  10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110
```

Leu Trp Glu Thr Gln Leu Gly Leu Ala Phe Leu Arg Gly Leu Ser Tyr
            115                 120                 125

His Asp Gly Ala Leu Val Val Thr Lys Ala Gly Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
                180                 185                 190

Ser Ser Arg Val Trp Trp Asp Ser Ser Phe Leu Gly Val Val His
            195                 200                 205

Leu Glu Ala Gly Glu Glu Val Val Arg Val Leu Asp Glu Arg Leu
            210                 215                 220

Val Arg Leu Arg Asp Gly Thr Arg Ser Tyr Phe Gly Ala Phe Met Val
225                 230                 235                 240

<210> SEQ ID NO 2
<211> LENGTH: 283
<212> TYPE: PRT
<213> ORGANISM: Homo sapiens

<400> SEQUENCE: 2

Met Glu Pro Pro Gly Asp Trp Gly Pro Pro Trp Arg Ser Thr Pro
1               5                   10                  15

Lys Thr Asp Val Leu Arg Leu Val Leu Tyr Leu Thr Phe Leu Gly Ala
                20                  25                  30

Pro Cys Tyr Ala Pro Ala Leu Pro Ser Cys Lys Glu Asp Glu Tyr Pro
            35                  40                  45

Val Gly Ser Glu Cys Cys Pro Lys Cys Ser Pro Gly Tyr Arg Val Lys
50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
                100                 105                 110

Arg Thr Glu Asn Ala Val Cys Gly Cys Ser Pro Gly His Phe Cys Ile
            115                 120                 125

Val Gln Asp Gly Asp His Cys Ala Ala Cys Arg Ala Tyr Ala Thr Ser
130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
                180                 185                 190

Gly Ala Gly Thr Ser Ser Ser His Trp Val Trp Trp Phe Leu Ser Gly
            195                 200                 205

Ser Leu Val Ile Val Ile Val Cys Ser Thr Val Gly Leu Ile Ile Cys
            210                 215                 220

Val Lys Arg Arg Lys Pro Arg Gly Asp Val Val Lys Val Ile Val Ser
225                 230                 235                 240

```
Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
            260                 265                 270

Ile Pro Ser Phe Thr Gly Arg Ser Pro Asn His
        275                 280

<210> SEQ ID NO 3
<211> LENGTH: 435
<212> TYPE: PRT
<213> ORGANISM: Homo sapiens

<400> SEQUENCE: 3

Met Leu Leu Pro Trp Ala Thr Ser Ala Pro Gly Leu Ala Trp Gly Pro
1               5                   10                  15

Leu Val Leu Gly Leu Phe Gly Leu Leu Ala Ala Ser Gln Pro Gln Ala
            20                  25                  30

Val Pro Pro Tyr Ala Ser Glu Asn Gln Thr Cys Arg Asp Gln Glu Lys
        35                  40                  45

Glu Tyr Tyr Glu Pro Gln His Arg Ile Cys Cys Ser Arg Cys Pro Pro
    50                  55                  60

Gly Thr Tyr Val Ser Ala Lys Cys Ser Arg Ile Arg Asp Thr Val Cys
65                  70                  75                  80

Ala Thr Cys Ala Glu Asn Ser Tyr Asn Glu His Trp Asn Tyr Leu Thr
                85                  90                  95

Ile Cys Gln Leu Cys Arg Pro Cys Asp Pro Val Met Gly Leu Glu Glu
            100                 105                 110

Ile Ala Pro Cys Thr Ser Lys Arg Lys Thr Gln Cys Arg Cys Gln Pro
        115                 120                 125

Gly Met Phe Cys Ala Ala Trp Ala Leu Glu Cys Thr His Cys Glu Leu
    130                 135                 140

Leu Ser Asp Cys Pro Pro Gly Thr Glu Ala Glu Leu Lys Asp Glu Val
145                 150                 155                 160

Gly Lys Gly Asn Asn His Cys Val Pro Cys Lys Ala Gly His Phe Gln
                165                 170                 175

Asn Thr Ser Ser Pro Ser Ala Arg Cys Gln Pro His Thr Arg Cys Glu
            180                 185                 190

Asn Gln Gly Leu Val Glu Ala Ala Pro Gly Thr Ala Gln Ser Asp Thr
        195                 200                 205

Thr Cys Lys Asn Pro Leu Glu Pro Leu Pro Pro Glu Met Ser Gly Thr
    210                 215                 220

Met Leu Met Leu Ala Val Leu Leu Pro Leu Ala Phe Phe Leu Leu Leu
225                 230                 235                 240

Ala Thr Val Phe Ser Cys Ile Trp Lys Ser His Pro Ser Leu Cys Arg
                245                 250                 255

Lys Leu Gly Ser Leu Leu Lys Arg Arg Pro Gln Gly Glu Gly Pro Asn
            260                 265                 270

Pro Val Ala Gly Ser Trp Glu Pro Pro Lys Ala His Pro Tyr Phe Pro
        275                 280                 285

Asp Leu Val Gln Pro Leu Leu Pro Ile Ser Gly Asp Val Ser Pro Val
    290                 295                 300

Ser Thr Gly Leu Pro Ala Ala Pro Val Leu Glu Ala Gly Val Pro Gln
305                 310                 315                 320

Gln Gln Ser Pro Leu Asp Leu Thr Arg Glu Pro Gln Leu Glu Pro Gly
                325                 330                 335
```

```
Glu Gln Ser Gln Val Ala His Gly Thr Asn Gly Ile His Val Thr Gly
            340                 345                 350

Gly Ser Met Thr Ile Thr Gly Asn Ile Tyr Ile Tyr Asn Gly Pro Val
            355                 360                 365

Leu Gly Gly Pro Pro Gly Pro Gly Asp Leu Pro Ala Thr Pro Glu Pro
    370                 375                 380

Pro Tyr Pro Ile Pro Glu Glu Gly Asp Pro Gly Pro Pro Gly Leu Ser
385                 390                 395                 400

Thr Pro His Gln Glu Asp Gly Lys Ala Trp His Leu Ala Glu Thr Glu
                405                 410                 415

His Cys Gly Ala Thr Pro Ser Asn Arg Gly Pro Arg Asn Gln Phe Ile
            420                 425                 430

Thr His Asp
        435
```